United States Patent [19]
Yong Cho et al.

[11] Patent Number: 5,998,442
[45] Date of Patent: Dec. 7, 1999

[54] BENZO [B] THIOPHENE COMPOUNDS, AND COMPOSITIONS FOR TREATING BONE LOSS, AND HYPERLIPIDEMIA

[75] Inventors: Stephen Sung Yong Cho, Palo Alto, Calif.; Timothy Alan Grese, Indianapolis, Ind.; Lewis Dale Pennington, Irvine, Calif.

[73] Assignee: Eli Lilly and Company, Indianapolis, Ind.

[21] Appl. No.: 08/924,771

[22] Filed: Aug. 27, 1997

Related U.S. Application Data

[60] Provisional application No. 60/025,160, Aug. 29, 1996.

[51] Int. Cl.$^6$ .................... A61K 31/445; C07D 409/12
[52] U.S. Cl. .................... 514/324; 514/212; 514/238.8; 514/319; 514/428; 514/609; 514/651; 540/609; 544/106; 546/202; 548/576; 549/51; 549/58
[58] Field of Search .................... 540/609; 544/106; 546/202; 548/576; 549/51, 58; 514/212, 238.8, 319, 324, 428, 609, 651

[56] References Cited

U.S. PATENT DOCUMENTS

| | | | |
|---|---|---|---|
| 3,394,125 | 7/1968 | Crenshaw | 548/525 |
| 3,413,305 | 11/1968 | Crenshaw | 548/525 |
| 4,133,814 | 1/1979 | Jones et al. | 548/525 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,798 | 1/1996 | Bryant et al. | 514/324 |

FOREIGN PATENT DOCUMENTS

| | | |
|---|---|---|
| 0 062 503 | 10/1982 | European Pat. Off. . |
| 0 617 030 | 9/1994 | European Pat. Off. . |
| 0 641 791 | 3/1995 | European Pat. Off. . |
| 0 675 121 | 10/1995 | European Pat. Off. . |
| 0 699 673 | 3/1996 | European Pat. Off. . |
| 89/0289 | 4/1989 | WIPO . |
| 95/10513 | 4/1995 | WIPO . |

OTHER PUBLICATIONS

Grese et al. "Structure–activity relationship of selective estrogen . . . " CA 126:74703, 1997.
Grese et al., "Structure–activity relationship of selective estrogen . . . " CA 126:74703, 1997.
Crenshaw, R.R., et al, *J. Med. Chem.* 14 (12):1185–1190 (1971).
Jones, C.D., et al, *J. Med. Chem.* 27 : 1057–1066, 1984.
Jones, C.D., et al, *J. Med. Chem.* 35: 931–938 1992.

*Primary Examiner*—Ceila Chang
*Attorney, Agent, or Firm*—Gilbert T. Voy

[57] ABSTRACT

The invention provides benzo[b]thiophene compounds, formulations, and methods of inhibiting bone loss or bone resorption, particularly osteoporosis, and cardiovascular-related pathological conditions including hyperlipidemia and related cardiovascular pathologies.

28 Claims, No Drawings

BENZO [B] THIOPHENE COMPOUNDS, AND COMPOSITIONS FOR TREATING BONE LOSS, AND HYPERLIPIDEMIA

This application claims the benefit of U.S. Provisional Application No. 60/025,160, filed Aug. 29, 1996.

BACKGROUND OF THE INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

In response to the clear need for new pharmaceutical agents which are capable of alleviating the symptoms of, inter alia, postmenopausal syndrome, the instant invention provides benzo[b]thiophene compounds, pharmaceutical formulations thereof, and methods of using such compounds for the treatment of postmenopausal syndrome and other estrogen-related pathological conditions such as those mentioned below.

Thus, it would be a significant contribution to the art to provide novel benzo[b]thiophene compounds useful, for example, in the inhibition, treatment, or prevention of the disease states as indicated herein.

SUMMARY OF THE INVENTION

The instant invention provides compounds of formula I:

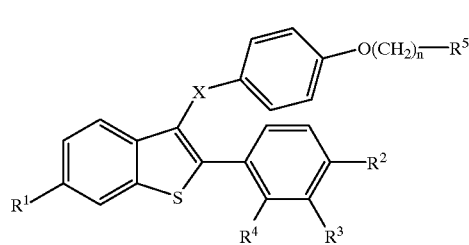

wherein:

X is —CH$_2$—, —CH(OH)—, or —CO—;

R$^1$ is —H, —OH, —O(C$_1$–C$_4$ alkyl), —OCOAr where Ar is phenyl or substituted phenyl, —OCO(C$_1$–C$_6$ alkyl), or —OSO$_2$(C$_4$–C$_6$ alkyl);

R$^2$, R$^3$, and R$^4$ are, independently, —R$^1$, —F, —Cl, C$_1$–C$_4$ alkyl, or —CF$_3$, with the proviso that R$^3$ and R$^4$ are not both hydrogen unless R$^2$ is CF$_3$, with the further proviso that when X is —CH$_2$—, then R$^3$ is —H, —Cl, —F, C$_1$–C$_4$ alkyl, or CF$_3$; n is 2 or 3; and R$^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt or solvate thereof.

The instant invention also provides compounds of formula VII which are useful as intermediates for the synthesis of compounds of formula I:

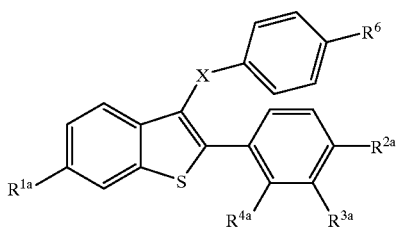

VII wherein:
X is —CO—, —CHOH—, or —CH$_2$—;
R$^{1a}$ is —H or —OR$^7$, where R$^7$ is a hydroxy protecting group;
R$^{2a}$, R$^{3a}$, R$^{4a}$ are, independently, —H, —OR$^7$, —F, —Cl, C$_1$–C$_4$ alkyl, or —CF$_3$, with the proviso that R$^{3a}$ and R$^{4a}$ are not both hydrogen unless R$^{2a}$ is CF$_3$, and with the further proviso that when X is —CH$_2$—, then R$^3$ is —H, —Cl, —F, C$_1$–C$_4$ alkyl, or CF$_3$; and
R$^6$ is —OCH$_3$ or —OH.

The instant invention also provides compounds of formula IX, which are useful in the synthesis of compounds of formula I:

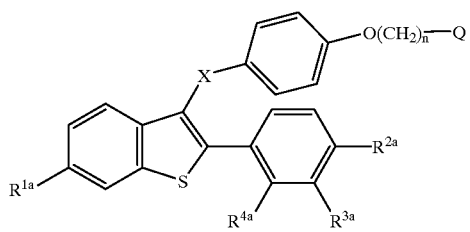

IX wherein:
R$^{1a}$, R$^{2a}$, R$^{3a}$, R$^{4a}$, n, and X have their previous meanings and provisions, and Q is a leaving group.

Further, the instant invention also provides compounds of formula XI, which are useful for the synthesis of compounds of formula I:

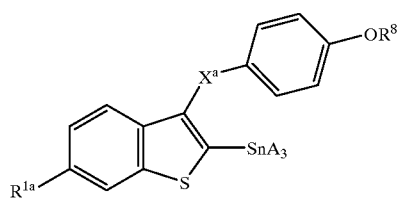

XI wherein:
X$^a$ is —CO—;
R$^{1a}$ has its previous meaning;
R$^8$ is —CH$_3$ or —(CH$_2$)$_n$R$^5$ where n and R$^5$ have their previous meanings; and
A is C$_1$–C$_4$ alkyl or phenyl.

The instant invention further provides pharmaceutical formulations containing compounds of formula I, optionally containing an effective amount of an additional therapeutic agent selected from estrogen, progestin, bisphosphonate, PTH, and subcombinations thereof, and the use of said compounds and/or subcombinations at least for the inhibition of bone loss or bone resorption, particularly osteoporosis and cardiovascular-related pathological conditions including hyperlipidemia and related cardiovascular pathologies.

DETAILED DESCRIPTION OF THE INVENTION

General terms used in the description of compounds herein described bear their usual meanings. For example, "C$_1$–C$_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—OC$_1$–C$_4$ alkyl" represents a C$_1$–C$_4$ alkyl group attached through an oxygen such as, for example, methoxy, ethoxy, n-propoxy, isopropoxy, and the like. Of these C$_1$–C$_4$ alkoxy groups, methoxy is highly preferred.

The term "substituted phenyl" refers to a phenyl group having one or more substituents selected from the group consisting of C$_1$–C$_4$ alkyl, —OC$_1$–C$_4$ alkyl, hydroxy, nitro, chloro, fluoro, or tri(chloro or fluoro)methyl.

The term "hydroxy protecting group (R$^7$)" contemplates numerous functionalities used in the literature to protect a hydroxyl function during a chemical sequence and which can be removed to yield the phenol. Included within this group would be acyls, mesylates, tosylates, benzyl, alkylsilyloxys, —OC$_1$–C$_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred R$^7$ hydroxy protecting groups, particularly methyl and alkylsilyloxy, are essentially as described in Examples 2 and 3, infra.

The term "leaving group (Q)" means a chemical entity which is capable of being displaced by an amino function via an SN$_2$ reaction. Such reactions are well known in the art and such groups would include halogens, mesylates, tosylates, and the like. A preferred leaving group would be bromo.

The compounds of this invention are derivatives of centrally located carbon, for example, the "—CO—", "—CHOH—", or "—CH$_2$—" moiety in formula I are therefore derivatives of methanones, methanols, or methanes. For example, a compound of A—CO—B, would be named [A][B]methanone. Further, the compounds of formula I are derivatives of benzo[b]thiophene which is named and numbered according to the Ring Index, The American Chemical Society, as follows:

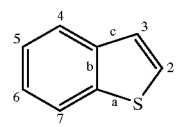

Several synthetic pathways are available for preparing the compounds of the instant invention. The first synthetic route is illustrated in Scheme I, below. The route is similar to that described in U.S. Pat. No. 5,420,349, which is herein incorporated by reference.

Scheme I
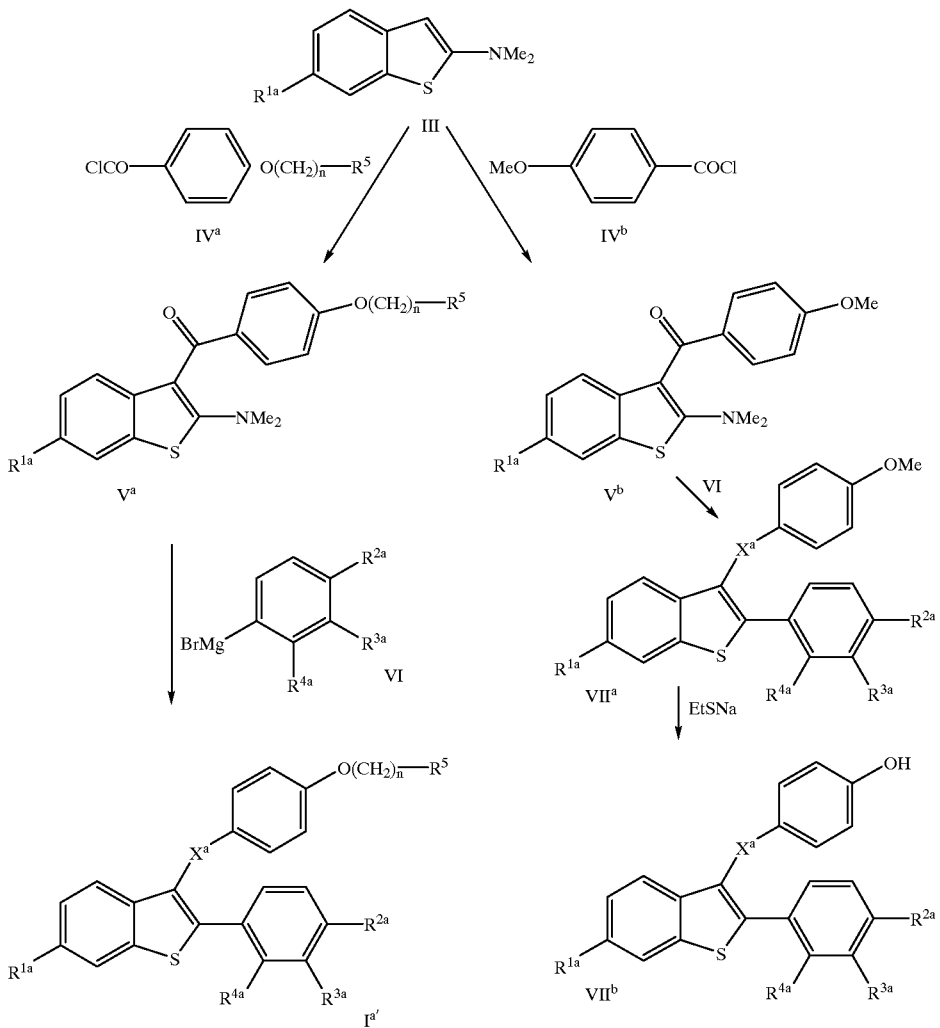
wherein:
$X^a$ is —CO—; and
$R^{1a}, R^{2a}, R^{3a}, R^{4a}, R^5$, and n have their previous meanings.
The starting material for the first synthetic route for the preparation of the compounds of the instant invention, is a 2-aminobenzothiophene of formula III. Its preparation and structure are provided below.
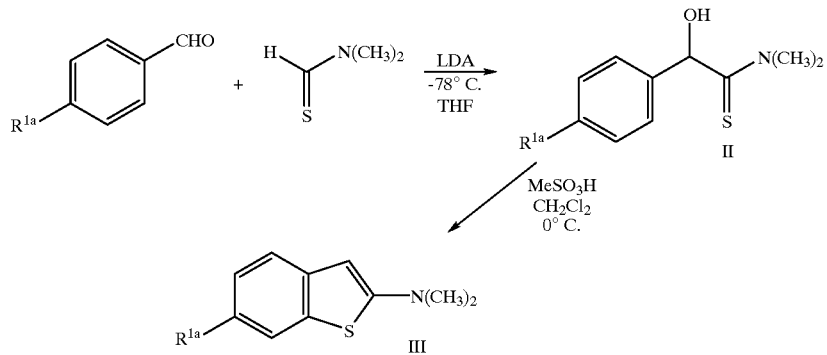
wherein: $R^{1a}$ is —H or —OCH$_3$ The synthesis of compound III, where $R^{1a}$ is methoxy, is also described in Ablenas, et al., *Can. J. Chem.*, 65, 1800–1803 (1987), the disclosure of which is herein incorporated by reference. The compounds of formula III are coupled with an acid chloride of formula $IV^a$ or $IV^b$ to form the intermediate keto-benzo[b]thiophenes, $V^a$ or $V^b$. This coupling reaction is a standard Friedel-Crafts acylation and is catalyzed by either a Lewis acid or a proton acid, a preferred Lewis acis is $AlCl_3$. This reaction may be carried out in a variety of inert solvents, such as halogenated hydrocarbons, ethers, and the like. This reaction may be run at a variety of temperatures, usually, between 25–150° C. and the reaction is complete within one to twenty hours, depending on the exact conditions (Olah, G., "Friedel-Crafts and Related Reactions", Interscience Publications, New York, London, and Sidney, 1963, Vol. I, Ch. III and IV). Preferred conditions for the current invention would utilize chlorobenzene as a solvent, a reaction temperature of 100–105° C. The reaction is completed in about nine hours. Compound $IV^b$ is commercially available. The compounds of formula $IV^a$ may be prepared via the methods described in U.S. Pat. Nos. 4,133,814, 4,380,635, and 4,418,068, the disclosure of which is herein incorporated by reference.

Briefly, 4-hydroxybenzoic acid is O-alkylated on the phenolic hydroxyl with a compound, $R^5(CH_2)_nCl$ (Br), in the presence of a strong base, such as, $K_2CO_3$, $CsCO_3$, NaH, and the like. Such reactions are usually run in an inert solvent such as, for example, THF, DMF, ether, and the like, at temperatures between 25–150° C. The O-alkylated benzoic acid product is converted to its acid chloride by treatment with a chlorinating agent, such as thionyl chloride. Compound $IV^a$ may be used as its free base or as a salt.

The first synthetic pathway continues with the reaction $V^a$ or $V^b$ with Grignard reagent of formula VI. This reaction is a 1,4 addition on the 3-ketone with elimination of the 2-amino. The preferred bromo Grignard reagents may be prepared by reacting the bromo derivatives of a formula VI compound with magnesium at ambient temperature in ether. The bromo precursors of formula VI compounds are either commercially available or can be obtained from methods known in the art. Such compounds of formula VI would include, but not be limited to: 1-bromo-2-methoxybenzene, 1-bromo-3-methoxybenzene, 1-bromo-2-ethylbenzene, 1-bromo-3-methylbenzene, 1-bromo-2,4-difluorobenzene, 1-bromo-3-chlorobenzene, 1-bromo-2-chlorobenzene, 1-bromo-2-fluorobenzene, 2-bromo-4-fluoroanisole, 4-bromo-2-fluoroanisole, and the like. The addition reaction may be run at temperatures between 25° and −78° C. in inert solvents, such as THF, ethyl ether, dioxane, and the like. The reaction of $V^a$ with VI yields, directly, a subset ($I^{a'}$) of the compounds of formula I, such as, for example, the compounds where X is the carbonyl and analogs where the hydroxyls, if present, are protected. The compounds of $I^{a'}$ may converted to other compounds of formula I via chemistry described below.

The reaction of $V^b$ with VI, yielding the intermediate compounds $VII^a$, is accomplished in the same manner as described, supra. Compounds $VII^a$ are converted to a versatile intermediate, $VII^b$, by the specific cleavage of the 4-methoxy of the benzoyl side-chain to the phenol. This cleavage is specific for the benzoyl-methoxy, even in the presence of other aromatic methoxyl groups in the molecule. This cleavage is described in the references cited and in Jones, C. D., et al., *J. Med. Chem.*, 1984 (27), p.1057, the disclosure of which is herein incorporated by reference. This cleavage reaction is facilitated by the use of NaSEt in an appropriate solvent, for example, DMF, at 80–100° C.

An alternate synthetic route for compounds of formula I is illustrated in Scheme Ia, below. This synthetic pathway begins with a compound of formula $VII^b$ and culminates with the formation of the useful intermediates of formula IX. As can be seen in Scheme Ia, there are two pathways to the compounds $IX^b$ and $IX^c$, for example, O-alkylation followed by reduction or reduction followed by O-alkylation. The sequence of these steps is not limited. It should be noted that in the compounds of formula $VII^d$ and $IX^c$, $R^{3b}$ may not be $-OR^7$. Attempts at reducing compounds $VII^{b-c}$ or $IX^{a-b}$ to the methylene with $R^{3b}$ having a ring activating group, for example, $-OR^7$, have not been successful by the methods described herein.

Scheme Ia

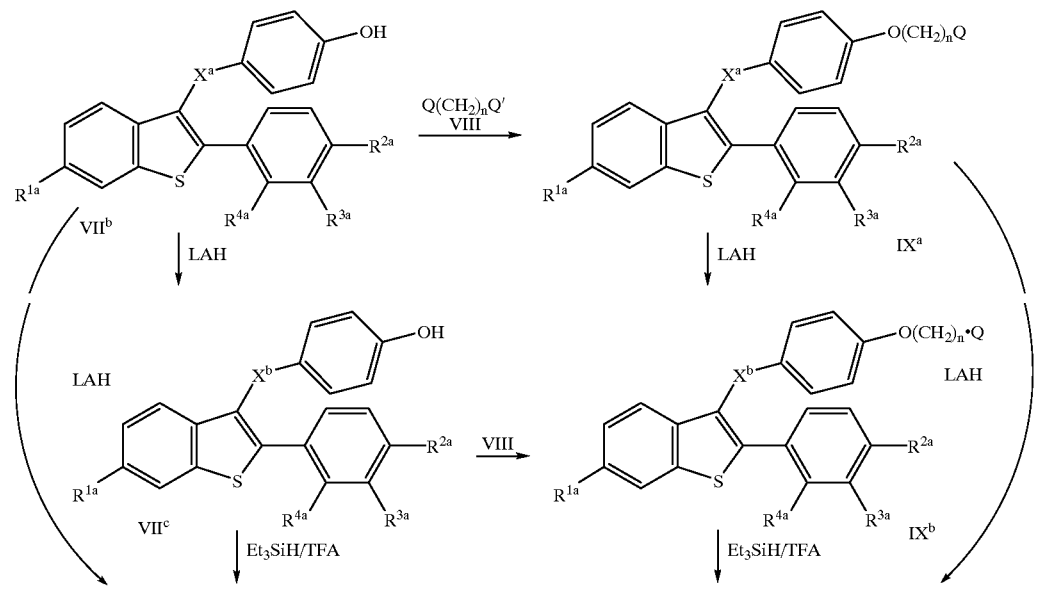

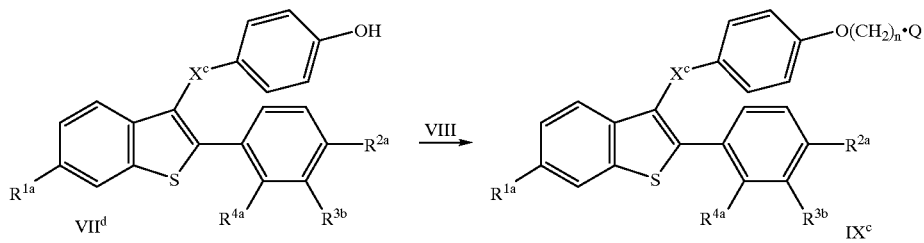

wherein
- $X^a$ is —CO—;
- $X^b$ is —CHOH—;
- $X^c$ is —CH$_2$—:
- $R^{1a}$, $R^{2a}$, $R^{3a}$, $R^{4a}$, and n have their previous meanings and provisions;
- $R^3b$ is —Cl, —F, —H, or —C$_1$–C$_4$ alkyl; and
- Q is a leaving group.

Alkylation of the 4-phenol is accomplished by the addition of an alkyl halide in the presence of a strong base. A compound of formula VIII may have Q and Q' as the same or different, preferred for the instant invention would be bromo for each. Thus, 1,2-dibromoethane or 1,3-dibromopropane are added to a compound of VII$^{b-d}$. Usually a two to five-fold molar excess to the dibromo reagent is used to minimize dimerization. The reaction is run in a compatable and inert solvent, such as, THF, DMF, ether, CHCl$_3$, and the like. The strong base required to facilitate the reaction is usually an inorganic base, such as, Na$_2$CO$_3$, K$_2$CO$_3$, Cs$_2$CO$_3$, and the like. The reaction is run at a variety of temperatures, usually between 25–150° C. and the time to complete the reaction is between six to eighteen hours, depending on the temperature and base used. The reaction progress may be monitored by conventional techniques, such as thin-layer chromatography (silica gel eluted EtOAc-hexane mixtures). Additionally, the reaction products may be purified by column chromatography utilizing the same system described above.

The reductions of the carbonyl and carbinol as outlined for the instant invention, supra, are described in U.S. Pat. No. 5,492,921, which is incorporated by reference, herein. Reduction of the carbonyl of VII$^b$ or IX$^a$ to the carbinol is accomplished with a hydride reagent, for example, LiAlH$_4$ (LAH), Na$_2$BH$_4$, and the like, in an inert solvent, such as ether, THF, toluene, and the like. The temperature of this reaction is important, if the desired product is only the carbinol, in that the use of a reagent such as LiAlH$_4$ at temperatures >100° C. leads to the reduction of the carbonyl to the methylene, such as VII$^d$ or IX$^c$. Temperatures in the range of 0–50° C. are adequate for the carbinol formation and the reaction time is usually between one and six hours. If the methylene compounds (VII$^d$ or IX$^c$) are desired, directly from the carbonyl precursors, then LAH at high temperature is an acceptable method, for example, LAH in chlorobenzene at reflux temperature (132° C.) for six to twelve hours. Again, as mentioned previously, the direct reduction of the carbonyl to methylene compounds with the high temperature-LAH method will lead to undesired by-products if $R^{3a}$ is an oxygen containing moiety, for example, —OR$^7$.

The carbinols (VII$^c$ and IX$^b$, where $R^{3a}$ is not —OR$^7$) are reduced to the methylene compounds by treatment with a strong acid protonating the carbinol and forming the carbocation by elimination of water. Subsequently, the carbocation is reduced by a hydrogen donating agent. In the instant invention a preferred strong acid would be trifluoroacetic acid and the hydrogen donating source would be a silane, particularly, trialkylsilanes and most preferred triethylsilane. This reaction may be run in CH$_2$Cl$_2$ at 0° C. and is complete within two hours.

The intermediate compounds IX$^{a-c}$ are converted to the compounds of formula I$^{a'-a'''}$ by displacement of the leaving group Q with an amine of R$^5$. This synthetic sequence is illustrated in Scheme Ib, below.

Scheme Ib

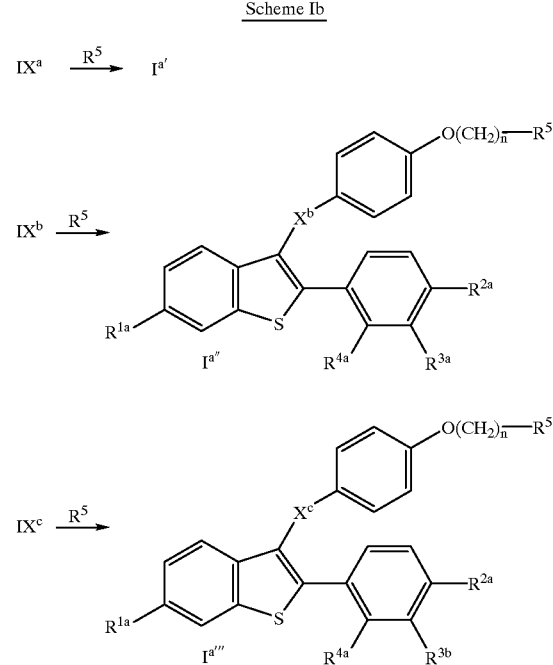

The displacement of the leaving group Q, especially the preferred bromo compound, with the amine R$^5$ is carried out in an appropriate, inert solvent, such as, ketones (acetone, methylethylketone, etc.), alcohols (methanol, ethanol, etc.), esters (methylacetate, ethylacetate, etc.), DMF, ethers (THF, ethylether, etc.), and the like. An acid scavenger (base) is used in equimolar amounts or in moderate excess, such bases would include Na$_2$CO$_3$, K$_2$CO$_3$, Cs$_2$CO$_3$, and the like. The displacement is carried out at ambient temperature or may be carried out at moderately elevated temperatures from about ambient temperature to the reflux temperature of the reaction mixture. Under these conditions, the reaction is usually complete within six to forty-eight hours; progress of the reaction may be monitored by standard chromatographic techniques An alternate synthesis of formula I compounds from those of VII$^{b-d}$ can be achieved by O-alkylation of the free phenol with a compound of formula X as seen in Scheme Ic.

Scheme Ic

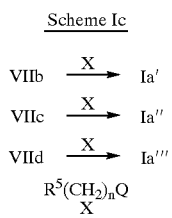

wherein R$^5$, n, and Q have their previous meanings, most preferred for Q would be chloro.

Methods for this O-alkylation are essentially the same as those described in forming compounds IX and IIIa, supra. In addition to the inorganic bases listed in the previous examples, this alkylation may be facilitated by the use of hydrides, such as, NaH, LiH, and the like. A preferred solvent for this alkylation using NaH would be anhydrous DMF.

The compounds of Ia' may be converted to those of Ia" and Ia'" via the reduction pathways outlined in Scheme Id, below.

Scheme Id

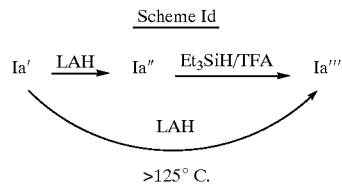

The chemistry involved in this pathway is the same as outlined, supra. As mentioned previously, in compounds Ia' and Ia" where R$^{3a}$ is —OR$^7$, can not be taken to the corresponding Ia'" via these methods.

An alternate chemical synthesis for the compounds of formula Ia' utilizes a palladium (O) coupling reaction with an organometallic and a phenylhalide, as illustrated in Scheme II, below.

Scheme II

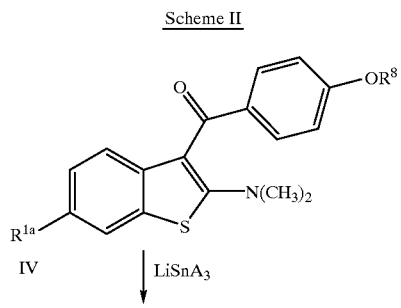

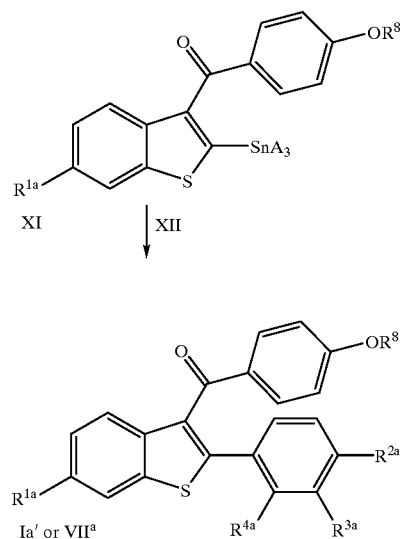

wherein:

R$^{1a-4a}$ have their previous meanings and provisions;

R$^8$ is —O(CH$_2$)$_n$R$^5$ or —OCH$_3$ where R$^5$ has its previous meaning; and A is C$_1$–C$_4$ alkyl.

A compound of formula IV is converted to its trialkylstannane (XI) by the addition of a trialkyltin-lithium complex. The tin-lithium complex is prepared by reaction of Li metal with a trialkylstannyl chloride. This complex is readily formed in an inert solvent such as, THF, ether, dioxane, and the like, at temperatures of 0–25° C. in several hours. The complex is added to a solution of compound IV in an inert solvent, for example, THF, ether, etc., at −78° C. and allowed to warm to ambient temperature for two to eight hours. A prefered group of XI compounds would be where A is methyl. The compounds of XI are allowed to react with a substituted phenyl bromide, XII (the same precursors as those used to make compounds VI, supra). This coupling is catalyzed with (Ph$_3$P)$_4$Pd in DMF at 100° C. in sixteen hours.

The compounds of formula XI are useful as intermediates for the preparation of the pharmacologically active compounds of the instant invention. Yet another synthetic pathway may be employed in the practice of the instant invention, which is illustrated in Scheme III, below. This sequence is similar to those provided in Jones, ibid.

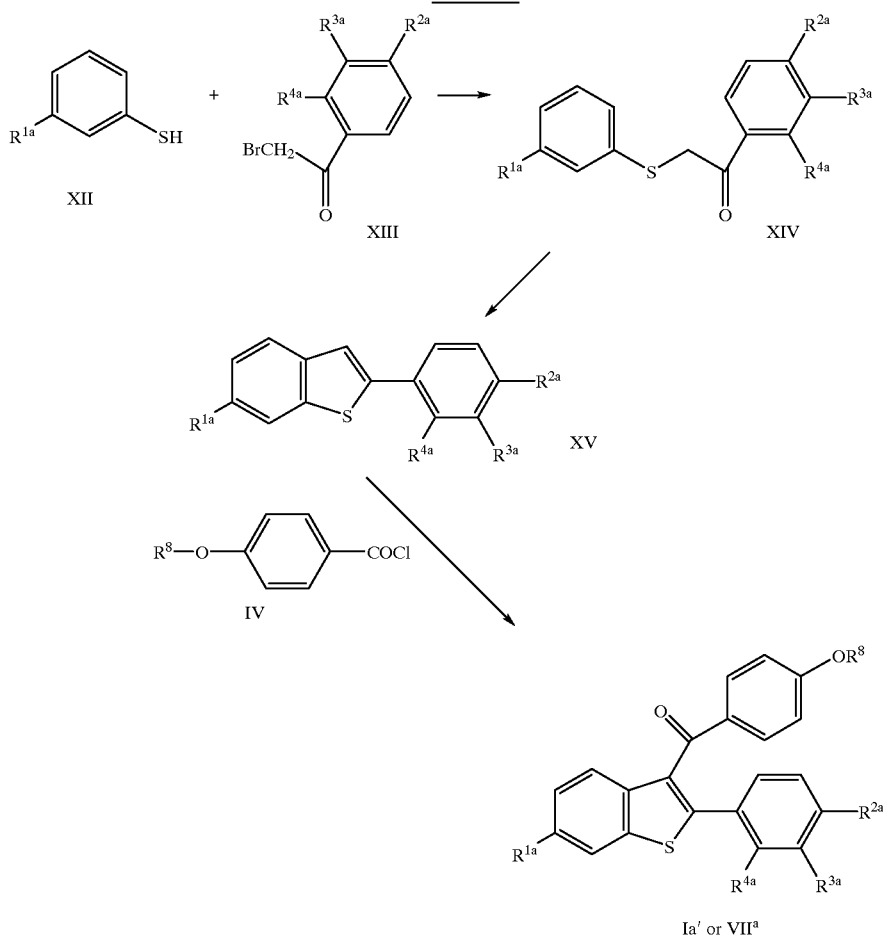

Scheme III wherein:

$R^{1a-4a}$ and $R^8$ have their previous meanings and provisions.

Briefly, a thiol (XII) and a substituted phenacyl bromide (XIII) are condensed in the presence of a strong base to form a keto-thioether compound of formula XIV. This reaction utilizes a base such as NaOH, KOH, $K_2CO_3$, and the like in a solvent such as anhydrous DMF. Alternatively, the solvent and base may be the same, for example, lutidines, pyridine, etc. The reaction is run at temperatures of 50–150° C. and usually are complete in six to eighteen hours. Compound XIV is cyclized and rearranged in a single reaction to XV, using a strong acid and high temperature, for example polyphosphoric acid at 100° C. for eighteen hours. Compound XV is acylated with a compound of formula IV to form either Ia', directly, or a compound of $VII^a$. This acylation is described, supra.

Compounds of formula Ia', Ia'', and Ia''' in which $R^7$, when present, is $C_1$–$C_4$ alkyl, preferably methyl, are pharmaceutically active for the methods described herein. Accordingly, such compounds are encompassed by the definition of compounds of formula I.

Compounds of formula Ia', Ia'', Ia''' would include, but not be limited to:

[2-(3-fluoro-4-methoxyphenyl)-6-methoxybenzo[b] thien-3-yl][4-[2-(1-piperidinyl)ethoxy]phenyl]methanone,

[2-(3-fluoro-4-hydroxyphenyl)-6-methoxybenzo[b]thien-3-yl][4-[2-(1-piperidinyl)ethoxy]phenyl]methanone,

[2-(3-chloro-4-methoxyphenyl)-6-methoxybenzo[b] thien-3-yl][4-[2-(1-piperidinyl)ethoxy]phenyl]methanone,

[2-(3-chloro-4-hydroxyphenyl)-6-methoxybenzo[b]thien-3-yl][4-[2-(1-piperidinyl)ethoxy]phenyl]methanone,

[2-(3-methyl-4-methoxyphenyl)-6-methoxybenzo[b] thien-3-yl][4-[2-(1-piperidinyl)ethoxy]phenyl]methanone,

[2-(3-methyl-4-hydroxyphenyl)-6-methoxybenzo[b] thien-3-yl][4-[2-(1-piperidinyl)ethoxy]phenyl]methanone,

[2-(3-methoxy-4-methoxyphenyl)-6-methoxybenzo[b] thien-3-yl][4-[2-(1-piperidinyl)ethoxy]phenyl]methanone,

[2-(3-fluoro-4-methoxyphenyl)-6-methoxybenzo[b] thien-3-yl][4-[2-(1-piperidinyl)ethoxy]phenyl]methanone,

[2-(2-methoxyphenyl)-6-methoxybenzo[b]thien-3-yl][4-[2-(1-piperidinyl)ethoxy]phenyl]methanone,

[2-(2-hydroxyphenyl)-6-methoxybenzo[b]thien-3-yl][4-[2-(1-piperidinyl)ethoxy]phenyl]methanone,

[2-(3-methoxyphenyl)-6-methoxybenzo[b]thien-3-yl][4-[2-(1-piperidinyl)ethoxy]phenyl]methanone,

[2-(3-hydroxyphenyl)-6-methoxybenzo[b]thien-3-yl][4-[2-(1-piperidinyl)ethoxy]phenyl]methanone,

[2-(3-fluoro-4-methoxyphenyl)benzo[b]thien-3-yl][4-[2-(1-piperidinyl)ethoxy]phenyl]methanone,

[2-(3-fluoro-4-methoxyphenyl)-6-methoxybenzo[b] thien-3-yl][4-[3-(1-piperidinyl)propoxy]phenyl]methanone,

[2-(3-fluoro-4-methoxyphenyl)-6-methoxybenzo[b] thien-3-yl][4-[2-(1-pyrrolidinyl)ethoxy]phenyl]methanone,

[2-(3-fluoro-4-methoxyphenyl)-6-methoxybenzo[b] thien-3-yl][4-[2-(N,N-diethylamino)ethoxy]phenyl] methanone,

[2-(3-fluoro-4-methoxyphenyl)-6-methoxybenzo[b]thien-3-yl][4-[2-(1-piperidinyl)ethoxy]phenyl]methanol,

[2-(3-fluoro-4-methoxyphenyl)-6-methoxybenzo[b]thien-3-yl][4-[2-(1-piperidinyl)ethoxy]phenyl]methane,

[2-(3-methoxyphenyl)-6-methoxybenzo[b]thien-3-yl][4-[2-(1-piperidinyl)ethoxy]phenyl]methane,

[2-(3-hydroxyphenyl)-6-methoxybenzo[b]thien-3-yl][4-[2-(1-piperidinyl)ethoxy]phenyl]methane,

[2-(3-chloro-4-methoxyphenyl)benzo[b]thien-3-yl][4-[3-(1-pyrrolidinyl)propoxy]phenyl]methane,

[2-(2-methyl-4-methoxyphenyl)-6-methoxybenzo[b]thien-3-yl][4-[2-(1-piperidinyl)ethoxy]phenyl]methanol,

[2-(3-fluorophenyl)-6-methoxybenzo[b]thien-3-yl][4-[2-(1-hexamethyleneimino)ethoxy]phenyl]methane,

[2-(3-methyl-4-methoxyphenyl)-6-methoxybenzo[b]thien-3-yl][4-[2-(1-morpholino)ethoxy]phenyl]methanone,

[2-(2-ethyl-4-methoxyphenyl)-6-methoxybenzo[b]thien-3-yl][4-[2-(1-piperidinyl)ethoxy]phenyl]methanone, and the like.

Hydroxy compounds of formula I are obtained by cleaving, when present, the $R^7$ hydroxy protecting group of formula Ia', Ia", and Ia''' compounds via well known procedures. Numerous reactions for the formation and removal of such protecting groups are described in a number of standard works including, for example, *Protective Groups in Organic Chemistry*, Plenum Press (London and New York, 1973); Green, T. W., Protective Groups in *Organic Synthesis*, Wiley, (New York, 1981); and *The Peptides*, Vol. I, Schrooder and Lubke, Academic Press (London and New York, 1965). Methods for removing the preferred $R^7$ hydroxy protecting group, for example, methyl or alkylsilyl, are essentially as described in the Examples, infra.

Other preferred compounds of formula I are prepared by replacing the 6, 2', 3', and/or 4'-position hydroxy moieties, when present, with a moiety of the formula —O—CO—($C_1$–$C_6$ alkyl), —O—CO—phenyl, —OCO-substituted phenyl, or —O— $SO_2$—($C_2$–$C_6$ alkyl) via well known procedures. See, for example, U.S. Pat. Nos. 5,393,763 or 5,482,949, the disclosure of which is herein incorporated by reference.

For example, when an —O—CO($C_1$–$C_6$ alkyl), —OCO-substituted phenyl, or —O—CO—phenyl group is desired, a mono-, di-, tri-, or tetrahydroxy compound of formula Ia'-Ia''' is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrrolidinopyridine may be used. See, for example, Haslam et al., *Tetrahedron*, 36:2409–2433 (1980).

The instant reactions are carried out at moderate temperatures, in the range from about −25° C. to about 100° C., frequently under an inert atmosphere such as nitrogen gas. However, ambient temperature is usually adequate for the reaction to run.

Acylation of a 6, 4', 3', and/or 2'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

When a formula I compound is desired in which the 6, 4', 3', and/or 2'-position hydroxy group of a formula Ia'-Ia''' compound is converted to a group of the formula —O—$SO_2$—($C_2$–$C_6$ alkyl), the mono-, di-, or tri-, tetrahydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The hydroxy compounds also can be reacted with the appropriate sulfonic anhydride or mixed sulfonic anhydrides. Such reactions are carried out under conditions such as were explained above in the discussion of reactions with acid halides and the like.

Other compounds of formula I would include, but not be limited to:

[2-(3-benzoyloxyphenyl)-6-benzoyloxybenzo[b]thien-3-yl][4-[2-(1-piperidinyl)ethoxy]phenyl]methanone

[2-(3-benzoyloxyphenyl)-6-benzoyloxybenzo[b]thien-3-yl][4-[2-(1-piperidinyl)ethoxy]phenyl]methane

[2-(3-benzoyloxyphenyl)benzo[b]thien-3-yl][4-[2-(1-piperidinyl)ethoxy]phenyl]methanone

[2-(3-acetyloxyphenyl)-6-acetyloxybenzo[b]thien-3-yl][4-[2-(1-piperidinyl)ethoxy]phenyl]methanone

[2-(3-n-butylsulfonoyloxyphenyl)-6-n-butylsulfonoyloxybenzo[b]thien-3-yl][4-[2-(1-piperidinyl)ethoxy]phenyl]methanone

[2-(3-benzoyloxy-4-fluorophenyl)-6-benzoyloxybenzo[b]thien-3-yl][4-[2-(1-piperidinyl)ethoxy]phenyl]methanone

[2-(3-chlorophenyl)-6-benzoyloxybenzo[b]thien-3-yl][4-[2-(1-piperidinyl)ethoxy]phenyl]methane

[2-(2-benzoyloxyphenyl)-6-benzoyloxybenzo[b]thien-3-yl][4-[2-(1-piperidinyl)ethoxy]phenyl]methanone

[2-(3-benzoyloxyphenyl)-6-benzoyloxybenzo[b]thien-3-yl][4-[2-(1-pyrrolidinyl)ethoxy]phenyl]methanone

[2-(2-benzoyloxyphenyl)benzo[b]thien-3-yl][4-[2-(1-piperidinyl)ethoxy]phenyl]methanol

[2-(3-benzoyloxy-4-benzoyloxyphenyl)-6-benzoyloxybenzo[b]thien-3-yl][4-[2-(1-piperidinyl)ethoxy]phenyl]methanone

[2-(3-benzoyloxyphenyl)-6-benzoyloxybenzo[b]thien-3-yl][4-[2-(l-hexamethyleneimino)ethoxy]phenyl]methanol

[2-(2-methyl-3-butroyloxyphenyl)-6-butroyloxybenzo[b]thien-3-yl][4-[2-(1-piperidinyl)ethoxy]phenyl]methanone

[2-(3-ethylphenyl)-6-benzoyloxybenzo[b]thien-3-yl][4-[2-(1-piperidinyl)ethoxy]phenyl]methanone 2-(3-ethyl-4-benzoyloxyphenyl)-6-benzoyloxybenzo[b]thien-3-yl][4-[2-(1-piperidinyl)ethoxy]phenyl]methanone, and the like.

The term "solvate" represents an aggregate that comprises one or more molecules of the solute, such as a formula I compound, with one or more molecules of solvent. Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions including hyperlipidemia and related cardiovascular pathologies.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy.

The instant invention also provides methods for inhibiting estrogen deficient pathologies including, for example, lack of birth control, postmenopausal syndrome including, for example, osteoporosis, cardiovascular disease, restenosis, and hyperlipidemia, certain cancers in men such as protate cancer, acne, hirsutism, dysfunctional uterine bleeding, dysmenorrhea, and atrophic vaginitis comprising administering to a mammal in need of treatment an effective amount of a compound of formula I, and, optionally, an effective amount of a progestin. One of skill in the art will recognize that estrogenic agents have a multitude of applications for treating estrogen deficient pathologies well beyond those listed infra. The instant invention contemplates and encompasses such maladies although not specified by name.

Compounds of the current invention may also be used in conjunction with other mixed estrogen agonists/antagonists, especially those which demonstrate increased detrimental stimulation of uterine tissue, such as, for example, tamoxifene, droloxifene, nafoxidene, or clomiphene.

As a further embodiment of the invention, the compounds of formula I may be administered along with an effective amount of an additional therapeutic agent, including but not limited to estrogen, progestin, other benzothiophene compounds including raloxifene, bisphosphonate compounds such as alendronate and tiludronate, parathyroid hormone (PTH), including truncated and/or recombinant forms of PTH such as, for example, PTH (1–34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available. As used herein, the term "estrogen" includes compounds having estrogen activity and estrogen-based agents. Estrogen compounds useful in the practice of the instant invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-a-ethynyl estradiol (0.01–0.03 mg/day), mestranol (0.05–0.15 mg/day), and conjugated estrogenic hormones such as Premarin® (Wyeth-Ayerst; 0.2–2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera® (Upjohn; 2.5–10 mg/day), norethylnodrel (1.0–10.0 mg/day), and norethindrone (0.5–2.0 mg/day). A preferred estrogen-based compound is Premarin®, and norethylnodrel and norethindrone are preferred progestin-based agents. The method of administration of each estrogen- and progestin-based agent is consistent with that known in the art.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
| --- | --- |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
| --- | --- |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
| --- | --- |
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 0.1-1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1 M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

Formulation 6: Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.5 |
| Cab-O-Sil | 0.25 |

Formulation 7: Combination Capsule II

| Ingredient | Quantity (mg/capsule) |
| --- | --- |
| Active ingredient | 50 |
| Norethylnodrel | 5 |
| Avicel pR 101 | 82.50 |
| Starch 1500 | 90 |
| Silicon Oil | 2 |
| Tween 80 | 0.50 |

Formulation 8: Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1

[2-Dimethylamino-6-methoxybenzo[b]thiophene][4-[2-(1-piperidinyl)ethoxy]phenyl]methanone A solution of 10.3 g of 2-dimethylamino-6-methoxybenzo[b]thiophene (49.8 mmol) and 15.9 g of 4-(2-piperidinoethoxy)benzoyl chloride hydrochloride (52.3 mmol) in 100 mL of chlorobenzene was prepared and heated to 105° C. under a nitrogen atmosphere. The reaction was allowed to cool over a period of one hour. The solidified mixture was extracted with 60 mL of $Na_2CO_3$ solution, followed by 30 mL of water, and finally by 10 mL of 50% aqueous NaOH. The reaction mixture was partioned between 300 mL of $CH_2Cl_2$ and 100 mL of water. The organic layer was washed with 50% saturated $Na_2CO_3$ (40 mL) and evaporated to a thick dark oil. The product was purified by chromatography on a silica gel column eluted with a linear gradient beginning with $CH_2Cl_2$ and ending with $CH_2Cl_2$—MeOH (19:1)(v/v). This yielded 19.8 g of the title compound as a thick, dark oil. PMR: d 1.3–1.4 (m,2H), 1.5–16 (m,4H), 2.43 (m,4H), 2.70 (t, J=5.9 Hz, 2H), 2.76 (s, 6H), 3.70 (s, 3H), 4.07 (t, J=5.9 Hz, 2H), 6.73 (dd, J=8.9 2.4 Hz, 1H), 6.84 (d, 8.8 Hz, 2H), 7.03 (d, J=2.4 Hz, 1H), 7.29 (d, J=8.9 Hz, 1H), 7.76 9d, J=8.8 Hz, 2H); EA: Calc. for $C_{25}H_{30}N_2O_3S$: C, 68.46; H, 6.89; N, 6.39; S, 7.31 Found: C, 68.19; H, 6.98; N, 6.32; S, 7.35.

Preparation 2

[Trimethylstannyl-6-methoxybenzo[b]thien-3-yl][4-[2-(1-piperidinyl)ethoxy]phenyl]methanone Lithium metal (7.1 g, 102 mmol) was suspended in 100 mL of anhydrous THF and treated with 103 mL of 1M trimethylstannyl chloride (103 mmol) in THF dropwise at 0° C. After warming to ambient temperature, the mixture was allowed to stir overnight. An aliquot of the $Me_3SnLi$ solution prepared above (0.507 M in THF, 19.4 mL, 9.85 mmol) was added dropwise to a solution of [2-dimethylamino-6-methoxybenzo[b]thiophene][4-[2-(1-piperidinyl)ethoxy] phenyl]methanone (2.4 g, 5.47 mmol) in THF (48 mL) at −78° C. The mixture was allowed to warm slowly to ambient temperature over five hours and quenchedly rapidly by pouring into a mixture of ice-cold saturated $NH_4Cl$ (100 mL) and $CH_2Cl_2$ (100 mL). The layers were separated, the aqueous layer was extracted with $CH_2Cl_2$, and the combined organic layers were washed with saturated $NaHCO_3$, dried ($Na_2SO_4$) and concentrated to provide 3.1 g (102%) of the title compound as a brown oil. PMR: d 0.34 (s,9H), 1.4–1.6 (m, 2H), 1.6–1.8 (m, 4H), 2.6–2.8 (m, $H), 2.86 (m, 2H), 3.86 (s, 3H), 4.27 (m, 2H), 6.84 (dd, J=8.9, 2.3 Hz, 1H), 6.92 (d, J=8.7 Hz, 2H), 7.25 (m, 1H), 7.34 (d, J=2.4 Hz, 1H), 7.77 (d, J=8.6 Hz, 2H).

Example 1

[2-(3-fluoro-4-methoxyphenyl)-6-methoxybenzo[b]thien-3-yl][4-[2-(1-piperidinyl)ethoxy]phenyl]methanone

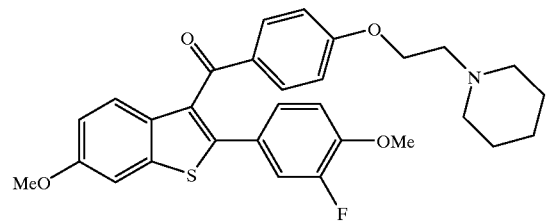

A solution of [2-dimethylamino-6-methoxybenzothien-3-yl][4-[2-(1-piperidinyl)ethoxy]phenyl]methanone (1.5 g, 3.6 mmol)(see U.S. Pat. No. 5,420,349) in chlorobenzene (15 mL) was cooled to 0° and treated with a 0.73 M THF solution of 3-fluoro-4-methoxyphenylmagnesium bromide (16.0 mL, 11.7 mmol)(prepared from 4-bromo-2-fluoroanisole, catalytic iodine, and magnesium turnings in THF). The mixture was allowed to warm to ambient temperature and when the starting material was consumed, the reaction was quenched with water and extracted with ethyl acetate. The organic layer was washed with water (2x), and brine (2x), dried (sodium sulfate), and concentrated. The residue was purified via chromatography (silica gel, 5–10% MeOH in $CH_2Cl_2$) to provide 0.79 g (44%) of the title compound as a brown oil: $^1H$ NMR d 1.44 (m, 2H), 1.59 (m, 4H), 2.48 (m, 4H), 2.74 (t, J=6.0 Hz, 2H), 3.83 (s, 3H), 3.88 (s, 3H), 4.09 (t, J=6.0 Hz, 2H), 6.77–6.83 (m, 3H), 6.96 (dd, J=2.3 Hz, 8.9 Hz, 1H), 7.11–7.19 (m, 2H), 7.31 (d, J=2.3 Hz, 1H), 7.50 (d, J=8.8 Hz, 1H), 7.75 (d, J=8.8 Hz, 2H); $^{13}C$ NMR d 24.4, 26.1, 55.3, 55.9, 56.4, 57.9, 66.5, 104.7, 113.5, 114.6, 115.3, 116.7, 117.0, 124.4, 125.5, 126.7, 126.8, 130.5, 131.6, 132.6, 134.1, 140.4, 140.9, 148.0, 148.1, 153.8, 158.1, 163.5, 193.2; MS (FD) m/e 519 ($M^+$); Anal. calc'd. for $C_{30}H_{30}FNO_4S$: C, 69.34; H, 5.82; N, 2.69. Found: C, 69.63; H, 5.89; N, 2.64.

Example 2

[2-(3-fluoro-4-hydroxyphenyl)-6-hydroxybenzo[b]thien-3-yl][4-[2-(1-piperidinyl)ethoxy]phenyl]methanone

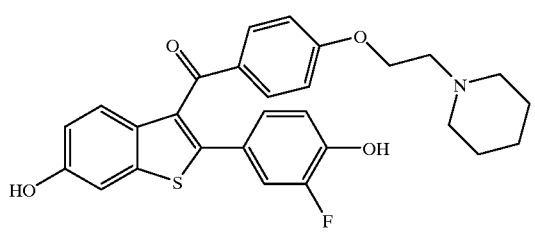

A solution of the product of Example 1 (0.65 g, 1.25 mmol), ethanethiol (0.46 mL, 6.32 mmol), and aluminum chloride (1.17 g, 8.78 mmol) in anhydrous $CH_2Cl_2$ (20 mL) was stirred for 3.5 h. The mixture was quenched with saturated sodium bicarbonate and extracted with ethyl acetate. The organic layer was washed with saturated sodium bicaronate and brine, dried (sodium sulfate), and concentrated. The residue was purified by chromatography (silica gel, 5–10% MeOH in $CH_2Cl_2$) and crystallized from MeOH/$CH_2Cl_2$ to give 240 mg (39%) of the title product as a yellow solid: $^1$H NMR (MeOD-$d_4$) d 1.62 (m, 2H), 1.80 (m, 4H), 3.11 (m, 4H), 3.34 (t, J=6.0 Hz, 2H), 4.32 (t, J=6.0 Hz, 2H), 4.86 (br s, 2H), 6.75 t, J=8.6 Hz, 1H), 6.88 (dd, J=2.2 Hz, 8.8 Hz, 1H), 6.92 (d, J=8.8 Hz, 2H), 6.97–7.06 (m, 3H), 7.27 (d, J=2.2 Hz, 1H), 7.43 (d, J=8.8 Hz, 1H), 7.73 (d, J=8.8 Hz, 2H); $^{13}$C NMR (DMSO-$d_6$) d 21.8, 23.1, 53.0, 63.4, 107.1, 114.6, 115.4, 115.7, 116.0, 118.1, 123.4, 124.2, 125.0, 130.0, 130.4, 131.8, 131.9, 138.9, 139.3, 145.3, 145.5, 148.9, 152.1, 155.7, 162.0, 192.3; MS (FD) m/e 492 (MH$^+$); Anal. calc'd. for $C_{28}H_{26}FNO_4S \cdot 0.75 H_2O$: C, 66.57; H, 5.65; N, 2.77. Found: C, 66.68; H, 5.78; N, 2.74.

Preparation 3

3-fluoro-4-(t-butyldimethylsilyloxy)bromobenzene

A solution of 4-bromo-3-fluorophenol (8.4 mL, 76.7 mmol) in dimethylformamide (30 mL) was treated with t-butyldimethylsilyl chloride (12.1 g, 80.5 mmol) and imidazole (11.0 g, 161 mmol). After 20 h, the mixture was diluted with ether, washed with water (2x) and brine (2x), dried ($Na_2SO_4$), and concentrated. Chromatography (silica gel, hexanes) provided the desired product as a clear oil: $^1$H NMR d 0.20 (s, 6H), 1.01 (s, 9H), 6.80 (t, J=8.8 Hz, 1H), 7.12 (m, 1H), 7.23 (m, 1H).

Preparation 4

[2-(3-fluoro-4-(t-butyldimethylsilyl)oxyphenyl)-6-methoxybenzo[b]thien-3-yl][4-[2-(1-piperidinyl)ethoxy]phenyl]methanone

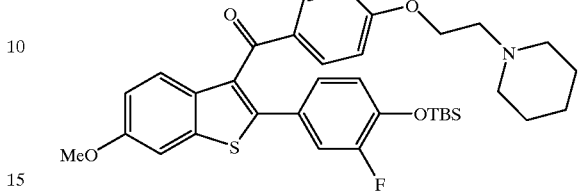

By the method described in Example 1, [2-dimethylamino-6-methoxybenzothien-3-yl][4-[2-(1-piperidinyl)ethoxy]phenyl]-methanone (3.7 g, 8.4 mmol) in THF (28 mL) was treated with a 0.9 M THF solution of 3-fluoro-(4-t-butyldimethylsilyloxy)-phenylmagnesium bromide (20 mL, 18 mmol) (prepared from the product of preparation 1, catalytic iodine, and magnesium powder in THF) to provide, after chromatography (silica gel, 5–10% MeOH in $CH_2Cl_2$) 3.72 g (75%) of the title compound as a yellow oil: $^1$H NMR d 0.12 (s, 6H), 0.96 (s, 9H), 1.43 (m, 2H), 1.59 (m, 4H), 2.48 (m, 4H), 2.74 (t, J=6.0 Hz, 2H), 3.87 (s, 3H), 4.07 (t, J=6.0 Hz, 2H), 6.70–6.77 (m, 3H), 6.96–7.14 (m, 3H), 7.32 (d, J=2.4 Hz, 1H), 7.59 (d, J=8.9 Hz, 1H), 7.73 (d, J=8.8 Hz, 2H); MS (FD) m/e, 619 (M$^+$); Anal. calc'd. for $C_{35}H_{42}FNO_4SSi$: C, 67.81; H, 6.83; N, 2.26. Found: C, 67.54; H, 6.85; N, 2.20.

Example 3

[2-(3-fluoro-4-hydroxyphenyl)-6-hydroxybenzo[b]thien-3-yl][4-[2-(1-piperidinyl)ethoxy]phenyl]methanone

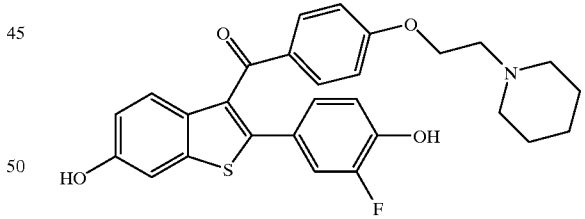

A solution of the product of Preparation 2 (3.5 g, 5.95 mmol), ethanethiol (1.3 mL, 17.85 mmol), and aluminum chloride (5.56 g, 41.7 mmol) in anhydrous $CH_2Cl_2$ (120 mL) was stirred for 1.5 h. The mixture was quenched with MeOH and water, stirred for 1 h, diluted with saturated sodium potassium tartrate and extracted with ethyl acetate. The organic layer was washed with saturated sodium potassium tartrate and brine, dried (sodium sulfate), and concentrated. The residue was purified by chromatography (silica gel, 5–10% MeOH in $CH_2Cl_2$) give 1.77 g of the desired compound as a yellow foam. Spectral data equivalent to Example 2.

Example 4

[2-(3-Chloro-4-methoxyphenyl)-6-methoxybenzo[b]thien-3-yl][4-[2-(1-piperidinyl)ethoxy]phenyl]methanone

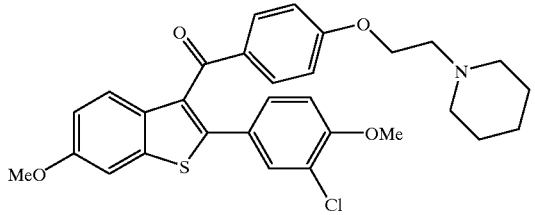

By the method described in Example 1, [2-dimethylamino-6-methoxybenzothien-3-yl][4-[2-(1-piperidinyl)ethoxy]phenyl]-methanone (1.0 g, 2.3 mmol) in chlorobenzene (10 mL) was treated with a 0.69 M THF solution of 3-chloro-4-methoxyphenylmagnesium bromide (11 mL, 7.6 mmol) (prepared from 4-bromo-2-chloroanisole, catalytic iodine, and magnesium turnings in THF) to provide, after chromatography (silica gel, 5–10% MeOH in $CH_2Cl_2$) 760 mg (62%) of the title compound as a yellow foam: $^1$H NMR d 1.43 (m, 2H), 1.58 (m, 4H), 2.73 (t, J=5.9 Hz, 2H), 3.82 (s, 3H), 3.87 (s, 3H), 4.08 (t, J=5.9 Hz, 2 ), 6.74 (d, J=9.2 Hz, 1H), 6.78 (d, J=9.2 Hz, 2H), 6.96 (dd, J=2.2 Hz, 8.9 Hz, 1H), 7.26 (dd, J=2.2 Hz, 8.7 Hz, 1H), 7.31 (d, J=2.1 Hz, 1H), 7.46 (d, J=2.1 Hz, 1H), 7.53 (d, J=8.9 Hz, 1H), 7.75 (d, J=8.7 Hz, 2H); $^{13}$C NMR d 24.4, 26.1, 55.3, 55.9, 56.4, 57.9, 66.4, 104.7, 112.2, 114.6, 115.3, 122.8, 124.5, 127.1, 128.8, 130.6, 130.8, 131.7, 132.5, 134.1, 140.4, 140.9, 155.3, 158.1, 163.4, 193.2; MS (FD) m/e 535 (M$^+$); Anal. calc'd. for $C_{30}H_{30}ClNO_4S$: C, 67.22; H, 5.64; N, 2.61. Found: C, 66.94; H, 5.90; N, 2.34.

Example 5

[2-(3-Chloro-4-hydroxyphenyl)-6-hydroxybenzo[b]thien-3-yl][4-[2-(1-piperidinyl)ethoxy]phenyl]methanone

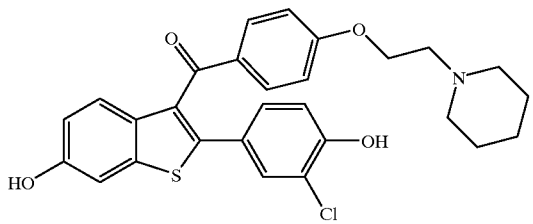

By the method described in Example 2, the product of Example 4 (0.61 g, 1.14 mmol), ethanethiol (0.42 mL, 5.77 mmol), and aluminum chloride (1.07 g, 8.03 mmol) were stirred in anhydrous $CH_2Cl_2$ (20 mL). After chromatography (silica gel, 5–10% MeOH in $CH_2Cl_2$) the remnant crystallized from MeOH/$CH_2Cl_2$ to give 343 mg (59%) of the title product as a yellow solid; $^1$H NMR d 1.33 (m, 2H), 1.44 (m, 4H), 2.37 (m, 4H), 2.48 (s, 1H), 2.60 (t, J=5.7 Hz, 2H), 4.06 (t, J=5.7 Hz, 2H), 6.83–6.93 (m, 4H), 7.12 (dd, J=2.0 Hz, 8.5 Hz, 1H), 7.25 (m, 2H), 7.33 (d, J=2.0 Hz, 1H), 7.63 (d, J=8.7 Hz, 2H), 9.82 (br s, 1H); $^{13}$C NMR (DMSO-d$_6$) d 23.8, 25.4, 54.2, 57.0, 65.9, 107.1, 114.5, 115.3, 116.6, 119.9, 123.5, 124.8, 128.2, 129.4, 129.5, 130.6, 131.7, 132.0, 138.5, 139.3, 153.5, 155.6, 162.9, 192.3; HRMS (FAB) m/e calc'd. for $C_{28}H_{27}ClNO_4S$ (MH$^+$): 508.1349, found: 508.1344.

Example 6

[2-(3-Methyl-4-methoxyphenyl)-6-methoxybenzo[b]thien-3-yl][4-[2-(1-piperidinyl)ethoxy]phenyl]methanone

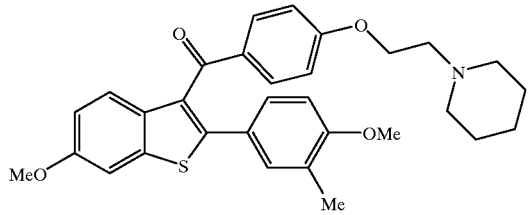

By the method described in Example 1, [2-dimethylamino-6-methoxybenzothien-3-yl][4-[2-(1-piperidinyl)ethoxy]phenyl]-methanone (1.0 g, 2.3 mmol) in chlorobenzene (10 mL) was treated with a 0.69 M THF solution of 3-methyl-4-methoxyphenylmagnesium bromide (11 mL, 7.6 mmol) (prepared from 4-bromo-2-methylanisole, catalytic iodine, and magnesium turnings in THF) to provide, after chromatography (silica gel, 5–10% MeOH in $CH_2Cl_2$) 810 mg (69%) of the title compound as a yellow oil: $^1$H NMR d 1.43 (m, 2H), 1.58 (m, 4H), 2.11 (s, 3H), 2.46 (m, 4H), 2.71 (t, J=5.8 Hz, 2H), 3.75 (s, 3H), 3.86 (s, 3H), 4.06 (t, J=5.8 Hz, 2H), 6.64 (d, J=8.9 Hz, 1H), 6.75 (d, J=8.6 Hz, 2H), 6.95 (d, J=8.9 Hz, 1H), 7.20 (s, 2H), 7.31 (s, 1H), 7.54 (d, J=8.9 Hz, 1H), 7.77 (d, J=8.6 Hz, 2H); $^{13}$C NMR d 16.4, 24.4, 26.1, 55.3, 55.6, 55.9, 57.9, 66.4, 104.8, 110.2, 114.5, 115.0, 124.3, 125.8, 127.1, 128.0, 130.6, 130.8, 131.6, 132.5, 134.3, 140.3, 143.2, 157.9, 158.3, 163.2, 193.6; MS (FD) m/e 515 (M$^+$); Anal. calc'd. for $C_{31}H_{33}NO_4S$: C, 72.21; H, 6.45; N, 2.72. Found: C, 72.43; H, 6.53; N, 2.95.

Example 7

[2-(3-Methyl-4-hydroxyphenyl)-6-hydroxybenzo[b]thien-3-yl][4-[2-(1-piperidinyl)ethoxy]phenyl]methanone

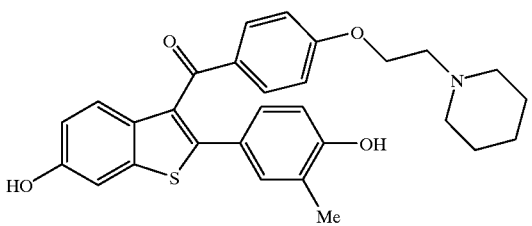

By the method described in Example 2, the product of Example 6 (640 mg, 1.24 mmol), ethanethiol (0.45 mL, 6.18 mmol), and aluminum chloride (1.16 g, 8.70 mmol) were stirred in anhydrous $CH_2Cl_2$ (20 mL). After chromatography (silica gel, 5–10% methznol in $CH_2Cl_2$), the remnant crystallized from MeOH/$CH_2Cl_2$ to give 386 mg (64%) of the title product as a yellow solid: $^1$H NMR (DMSO-d$_6$) d 1.34 (m, 2H), 1.44 (m, 4H), 2.37 (m, 4H), 2.60 (t, J=5.7 Hz, 2H), 4.05 (t, J=5.7 Hz, 2H), 6.64 (d, J=8.3 Hz, 1H), 6.82 (dd, J=2.1 Hz, 8.8 Hz, 1H), 6.89 (d, J=8.8 Hz, 2H), 6.96 (dd, J=2.1 Hz, 8.3 Hz, 1H), 7.05 (d, J=1.8 Hz, 1H), 7.22 (d, J=8.8

Hz, 1H), 7.30 (d, J=1.8 Hz, 1H), 7.61 (d, J=8.8 Hz, 2H), 9.62 (br s, 1H), 9.75 (br s, 1 H); $^{13}$C NMR (DMSO-d$_6$) d 15.7, 23.8, 25.4, 54.2, 57.0, 65.9, 107.0, 114.4, 114.8, 115.1, 123.2, 123.6, 124.3, 126.9, 129.5, 129.7, 130.6, 131.6 , 132.3, 139.1, 140.5, 155.3, 155.9, 162.7, 192.6; MS (FD) m/e 487 (M$^+$); Anal. calc'd. for C$_{29}$H$_{29}$NO$_4$S: C, 71.43; H, 6.00; N, 2.87. Found: C, 71.33; H, 6.05; N, 2.92.

Example 8

[2-(3,4-Dimethoxyphenyl)-6-methoxybenzo[b]thien-3-yl][4-[2-(1-piperidinyl)ethoxy]phenyl]methanone

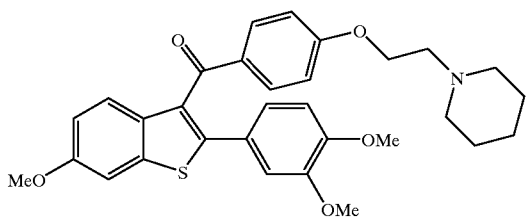

By the method described in Example 1, [2-dimethylamino-6-methoxybenzothien-3-yl][4-[2-(1-piperidinyl)ethoxy]phenyl]-methanone (1.64 g, 3.75 mmol) in THF (15 mL) was treated with a 0.63 M solution of 3,4-dimethoxyphenylmagnesium bromide (12.0 mL, 7.56 mmol) (prepared from 4-bromoveratrole, catalytic iodine, and magnesium turnings in THF). Purification by chromatography (silica gel, 5–10% MeOH in CH$_2$Cl$_2$) gave 1.32 g (66%) of the title compound as a yellow foam: $^1$H NMR d 1.45 (m, 2H), 1.61 (m, 4H), 2.48 (m, 4H), 2.75 (t, J=6.0 Hz, 2H), 3.74 (s, 3H), 3.84 (s, 3H), 3.90 (s, 3H), 4.09 (t, J=6.0 Hz, 2H), 6.76 (d, J=8.2 Hz, 1H), 6.77 (d, J=8.7 Hz, 2H), 6.91 (d, J=1.6 Hz, 1H), 6.98 (dd, J=2.2 Hz, 8.9 Hz, 1H), 7.04 (dd, J=1.6 Hz, 8.2 Hz, 1H), 7.33 (d, J=2.2 Hz, 1H), 7.57 (d, J=8.9 Hz, 1H), 7.79 (d, J=8.7 Hz, 2H); $^{13}$C NMR d 23.6, 25.3, 54.5, 55.1, 55.2, 55.3, 57.1, 65.6, 104.0, 110.6, 111.6, 113.7, 114.3, 121.0, 123.5, 125.7, 129.9, 130.1, 131.7, 133.4, 139.5, 141.8, 148.1, 148.7, 157.2, 162.5, 192.8; MS (FD) m/e 531 (M$^+$); Anal. calc'd. for C$_{31}$H$_{33}$NO$_5$S: C, 70.03; H, 6.26; N, 2.63. Found: C, 70.21; H, 6.36; N, 2.67.

Example 9

[2-(2-Methoxyphenyl)-6-methoxybenzo[b]thien-3-yl][4-[2-(1-piperidinyl)ethoxy]phenyl]methanone

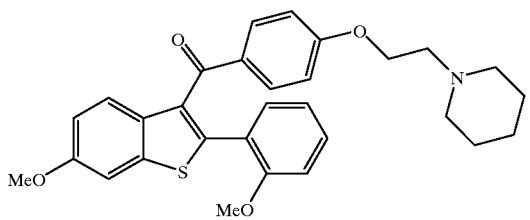

By the method described in Example 1, [2-dimethylamino-6-methoxybenzothien-3-yl][4-[2-(1-piperidinyl)ethoxy]phenyl]-methanone (1.0 g, 2.29 mmol) in chlorobenzene (10 mL) was treated with a 0.65 M THF solution of 2-methoxyphenylmagnesium bromide (11.0 mL, 7.11 mmol) (prepared from 2-bromoanisole, catalytic iodide, and magnesium turnings in THF) to provide after chromatography (silica gel, 5–10% MeOH in CH$_2$Cl$_2$) 710 mg (62%) of the title compound as a yellow foam: $^1$H NMR d 1.44 (m, 2H), 1.60 (m, 4H), 2.48 (m, 4H), 2.72 (t, J=5.9 Hz, 2H), 3.51 (s, 3H), 3.87 (s, 3H), 4.06 (t, J=5.9 Hz, 2H), 6.65 (d, J=8.2 Hz, 1H), 6.73 (d, J=8.6 Hz, 2H), 6.89 (t, J=7.4 Hz, 1H), 6.98 (d, J=8.9 Hz, 1H), 7.17 (t, J=7.7 Hz, 1H), 7.33 (s, 1H), 7.41 (d, J=7.4 Hz, 1H), 7.68 (d, J=8.9 Hz, 1H), 7.75 (d, J=8.6 Hz, 1H); $^{13}$C NMR d 23.6, 25.4, 54.0, 54.6, 55.1, 57.2, 65.6, 103.6, 104.9, 110.2, 113.2, 114.2, 120.1, 122.2, 124.1, 129.6, 130.1, 130.9, 131.5, 133.0, 139.3, 140.0, 155.3, 157.0, 161.9, 191.1; MS (FD) m/e 501 (M$^+$).

Example 10

[2-(2-Hydroxyphenyl)-6-hydroxybenzo[b]thien-3-yl][4-[2-(1-piperidinyl)ethoxy]phenyl]methanone

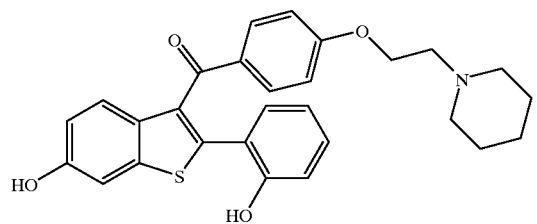

By the method described in Example 2, the product of Example 9 (560 mg, 1.12 mmol), ethanethiol (0.42 mL, 5.77 mmol), and aluminum chloride (1.05 g, 7.88 mmol) were stirred in anhydrous CH$_2$Cl$_2$ (30 mL) to provide, after chromatography (silica gel, 5–10% methznol in CH$_2$Cl$_2$), 257 mg (49%) of the title product as a yellow foam: $^1$H NMR d 1.47 (m, 2H), 1.62 (m, 4H), 2.54 (m, 4H), 2.75 (t, J=5.4 Hz, 2H), 4.10 (t, J=5.4 Hz, 2H), 4.87 (br s, 2H), 6.64 (d, J=8.1 Hz, 1H), 6.72–6.85 (m, 4H), 7.02 (m, 1H), 7.25 (m, 2H), 7.47 (d, J=8.9 Hz, 1H), 7.67 (d, J=8.6 Hz, 2H); MS (FD) m/e 473 (M$^+$); Anal. calc'd. for C$_{28}$H$_{27}$NO$_4$S: C, 71.01; H, 5.75; N, 2.96. Found: C, 71.27; H, 5.82; N, 3.19.

Example 11

[2-(3-Methoxyphenyl)-6-methoxybenzo[b]thien-3-yl][4-[2-(1-piperidinyl)ethoxy]phenyl]methanone

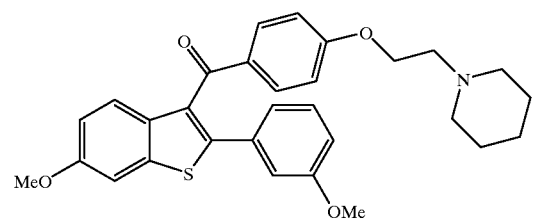

By the method described in Example 1, [2-dimethylamino-6-methoxybenzothien-3-yl][4-[2-(1-piperidinyl)ethoxy]phenyl]-methanone (1.0 g, 2.29 mmol) in chlorobenzene (10 mL) was treated with a 0.64 M THF solution of 3-methoxyphenylmagnesium bromide (11.0 mL, 7.04 mmol) (prepared from 3-bromoanisole, catalytic iodide, and magnesium turnings in THF) to provide after chromatography (silica gel, 5–10% MeOH in CH$_2$Cl$_2$) 610 mg (53%) of the title compound as a dark oil: $^1$H NMR d 1.44 (m, 2H), 1.59 (m, 4H), 2.47 (m, 4H), 2.73 (t, J=6.0 Hz, 2H), 3.70 (s, 3H), 3.88 (s, 3H), 4.08 (t, J=6.0 Hz, 2H), 6.76 (m, 3H), 6.96–7.04 (m, 3H), 7.15 (t, J=8.0 Hz, 1H), 7.33 (d, J=2.0 Hz, 1H), 7.56 (d, J=8.9 Hz, 1H), 7.78 (d, J=8.7 Hz, 2H); MS (FD) m/e 501 (M⁺); Anal. calc'd. for $C_{30}H_{31}NO_4S$: C, 71.83; H, 6.23; N, 2.79. Found: C, 71.68; H, 6.25; N, 2.66.

Preparation 5

3-(t-Butyldimethylsilyloxy)bromobenzene

By the method of preparation 1, 3-bromophenol (5.0 g, 28.90 mmol) in dimethylformamide (20 mL) was treated with t-butyldimethylsilyl chloride (4.4 g, 28.9 mmol) and imidazole (3.9 g, 57.9 mmol) to provide, after chromatography (silica gel, hexanes), the desired product as a clear oil: ¹H NMR d 0.22 (s, 6H), 1.00 (s, 9H), 6.78 (m, 1H), 7.02 (s, 1H), 7.10 (d, J=5.1 Hz, 2H); MS (FD) m/e 288 (M⁺); Anal. calc'd. for $C_{12}H_{19}BrOSi$: C, 50.17; H, 6.67. Found: C, 50.07; H, 6.45.

Preparation 6

[2-(3-(t-butyldimethylsilyl)oxyphenyl)-6-methoxybenzo[b]thien-3-yl][4-[2-(1-piperidinyl)ethoxy]phenyl]methanone

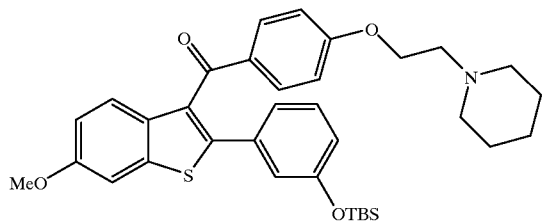

By the method described in Example 1, [2-dimethylamino-6-methoxybenzothien-3-yl][4-[2-(1-piperidinyl)ethoxy]phenyl]-methanone (1.6 g, 3.75 mmol) in THF (15 mL) was treated with a 0.6 M THF solution of 3-(t-butyldimethylsilyloxy)phenylmagnesium bromide (16 mL, 9.60 mmol) (prepared from the product of preparation 3, catalytic iodine, and magnesium turnings in THF) to provide, after chromatography (silica gel, 5–10% MeOH in $CH_2Cl_2$) 1.65 g (73%) of the title compound as a yellow oil: ¹H NMR d 0.11 (s, 6H), 0.95 (s, 9H), 1.45 (m, 2H), 1.61 (m, 4H), 2.50 (m, 4H), 2.76 (t, J=5.9 Hz, 2H), 3.89 (s, 3H), 4.09 (t, J=5.9 Hz, 2H), 6.69 (d, J=8.5 Hz, 1H), 6.77 (d, J=8.5 Hz, 2H), 6.90 (s, 1H), 6.96–7.10 (m, 3H), 7.34 (m, 1H), 7.55 (d, J=8.8 Hz, 1H), 7.78 (d, J=8.2 Hz, 2H); MS (FD) m/e 601 (M⁺); Anal. calc'd. for $C_{35}H_{43}NO_4SSi$: C, 69.85; H, 7.20; N, 2.33. Found: C, 69.83; H, 7.34; N, 2.34.

Example 12

[2-(3-Hydroxyphenyl)-6-hydroxybenzo[b]thien-3-yl][4-[2-(1-piperidinyl)ethoxy]phenyl]methanone

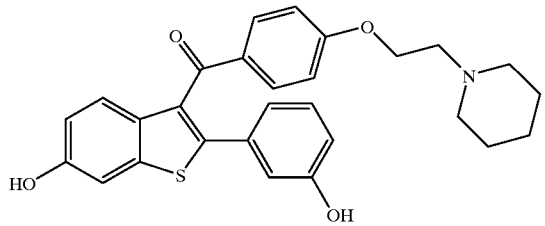

By the method described in Example 3, the product of Preparation 4 (1.6 g, 2.66 mmol), ethanethiol (0.95 mL, 13.04 mmol), and aluminum chloride (2.5 g, 18.75 mmol) were stirred in anhydrous $CH_2Cl_2$ (40 mL) to provide, after chromatography (silica gel, 5–10% MeOH in $CH_2Cl_2$), 1.2 g (95%) of the title product as a yellow foam: ¹H NMR (MeOD-d₄) d 1.45 (m, 2H), 1.59 (m, 4H), 2.50 (m, 4H), 2.72 (t, J=5.5 Hz, 2H), 4.11 (t, J=5.5 Hz, 2H), 4.88 (br s, 2H), 6.61 (m, 1H), 6.80–6.88 (m, 5H), 7.01 (t, J=8.1 Hz, 1H), 7.27 (d, J=2.1 Hz, 1H), 7.39 (d, J=8.8 Hz, 1H), 7.70 (d, J=8.7 Hz, 2H); ¹³C NMR (DMSO-d₆) d 23.8, 25.5, 54.2, 57.0, 65.9, 107.1, 114.5, 114.9, 115.4, 115.5, 118.9, 123.5, 129.5, 129.9, 131.1, 131.7, 132.0, 134.1, 139.1, 139.5, 155.8, 157.5, 162.9, 192.5; MS (FD) m/e 474 (MH⁺); HRMS (FAB) m/e calc'd. for $C_{28}H_{28}NO_4S$ (MH⁺): 474.1739, found: 474.1741; Anal. calc'd for $C_{28}H_{27}NO_4S$·0.75 $H_2O$: C, 69.04; H, 5.91; N, 2.91. Found: C, 68.86; H, 5.73; N, 2.61.

Example 13

[2-(3-Benzoyloxyphenyl)-6-benzoyloxybenzo[b]thien-3-yl][4-[2-(1-piperidinyl)ethoxy]phenyl]methanone

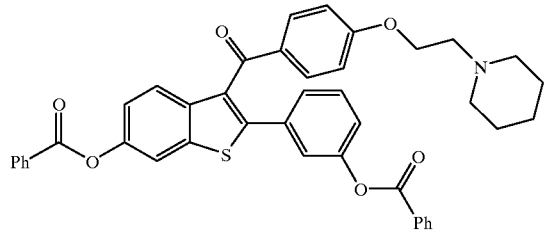

To a stirred solution of the product of Example 12 (0.50 g, 1.06 mmol) in anhydrous THF (20 mL) was added triethylamine (0.37 mL, 2.65 mmol) and benzoyl chloride (0.30 mL, 2.58 mmol). After >16 h, the mixture was diluted with ethyl acetate and washed with saturated sodium bicarbonate and brine. The organic layer was dried ($Na_2SO_4$), concentrated, and purified by chromatography (silica gel, 5% MeOH in $CH_2Cl_2$) to provide 0.67 g (93%) of the desired product as a white foam; ¹H NMR d 1.47 (m, 2H), 1.68 (m, 4H), 2.64 (m, 4H), 2.89 (t, J=5.6 Hz, 2H), 4.20 (t, J=5.6 Hz, 2H), 6.80 (d, J=8.8 Hz, 2H), 7.13 (m, 1H), 7.22–7.35 (m, 4H), 7.50–7.56 (m, 4H), 7.63–7.70 (m, 2H), 7.72–7.78 (m, 4H), 8.18 (d, J=7.3 Hz, 2H), 8.24 (m, J=7.8 Hz, 2H); MS (FD) m/e 681 (M⁺); Anal. calc'd. for $C_{42}H_{35}N_1O_6S_1$: C, 73.99; H, 5.17; N, 2.05. Found: C, 73.74; H, 5.26; N, 2.25.

Example 14

[2-(3-(1-butylsulfonyl)oxyphenyl)-6-(1-butylsulfonyl)oxybenzo[b]thien-3-yl][4-[2-(1-piperidinyl)ethoxy]phenyl]methanone

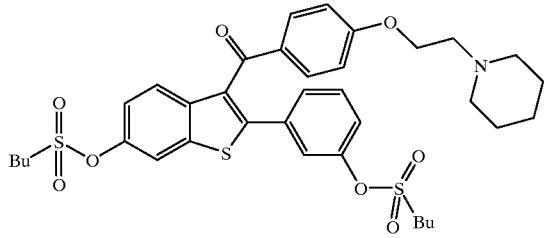

To a stirred solution of the product of Example 12 (0.50 g, 1.06 mmol) in anhydrous THF (20 mL) was added triethylamine (0.37 mL, 2.65 mmol) and 1-butanesulfonyl chloride (0.34 mL, 2.62 mmol). After >16 h the mixture was diluted with ethyl acetate and washed with saturated sodium bicarbonate and brine. The organic layer was dried ($Na_2SO_4$), concentrated, and purified via chromatography (silica gel, 5% MeOH in $CH_2Cl_2$) to provide 0.68 g (90%) of desired product as an oil: $^1$H NMR d 1.00 (dt, J=2.1 Hz, 7.3 Hz, 6H), 1.44–1.64 (m, 10H), 1.89–2.02 (m, 4H), 2.50 (m, 4H), 2.76 (t, J=5.9 Hz, 2H), 3.17 (m, 2H), 3.30 (m, 2H), 4.10 (t, J=5.9 Hz, 2H), 6.79 (d, J=8.8 Hz, 2H), 7.21–7.39 (m, 5H), 7.67–7.73 (m, 3H), 7.84 (d, J=2.1 Hz, 1H); MS (FD) m/e 713 ($M^+$); Anal. calc'd. for $C_{36}H_{43}N_1O_8S_3$: C, 60.57; H, 6.07; N, 1.96. Found: C, 60.28; H, 5.95; N, 1.89.

Example 15

[2-(2-Methyl-4-methoxyphenyl)-6-methoxybenzo[b]thien-3-yl][4-[2-(1-piperidinyl)ethoxy]phenyl]methanone

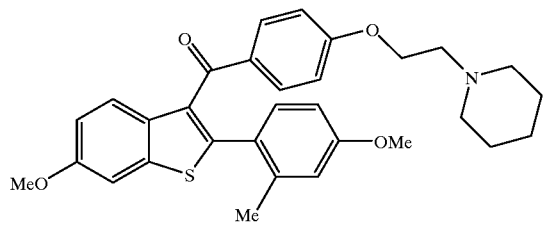

By the method described in Example 1, [2-dimethylamino-6-methoxybenzothien-3-yl][4-[2-(1-piperidinyl)ethoxy]phenyl]-methanone (1.6 g, 3.6 mmol) in THF (12 mL) was treated with a 0.65 M THF solution of 2-methyl-4-methoxyphenylmagnesium bromide (20 mL, 13.0 mmol) (prepared from 4-bromo-3-methylanisole, catalytic iodine, and magnesium turnings in THF) to provide, after chromatography (silica gel, 5–10% MeOH in $CH_2Cl_2$) 1.02 g (55%) of the title compound as a dark oil: $^1$H NMR d 1.46 (m, 2H), 1.63 (m, 4H), 2.26 (s, 3H), 2.54 (m, 4H), 2.79 (t, J=5.8 Hz, 2H), 3.47 (s, 3H), 3.89 (s, 3H), 4.12 (t, J=5.8 Hz, 2H), 6.60 (m, 2H), 6.74 (d, J=8.8 Hz, 2H), 6.98 (dd, J=2.4, 8.9 Hz, 1H), 7.19 (d, J=9.3 Hz, 1H), 7.32 (d, J=2.4 Hz, 1H), 7.60 (d, J=8.9 Hz, 1H), 7.69 (d, J=8.8 Hz, 2H); MS (FD) m/e 515 ($M^+$); Anal. calc'd. for $C_{31}H_{33}N_1O_4S_1$: C, 72.20; H, 6.45; N, 2.72. Found: C, 72.50; H, 6.56; N, 2.80.

Example 16

[2-(2-Methyl-4-hydroxyphenyl)-6-hydroxybenzo[b]thien-3-yl][4-[2-(1-piperidinyl)ethoxy]phenyl]methanone

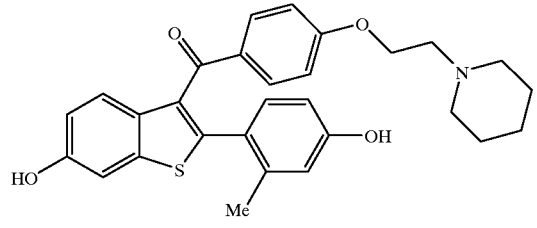

By the method described in Example 2, the product of Example 15 (1.0 g, 1.94 mmol), ethanethiol (0.71 mL, 9.75 mmol), and aluminum chloride (1.81 g, 13.57 mmol) were stirred in anhydrous $CH_2Cl_2$ (40 mL). Purification by chromatography (silica gel, 5–10% MeOH in $CH_2Cl_2$), provided 260 mg (27%) of the title product as a dark yellow foam: $^1$H NMR d 1.47 (m, 2H), 1.61 (m, 4H), 2.13 (s, 3H), 2.55 (m, 4H), 2.77 (t, J=5.5 Hz, 2H), 4.09 (t, J=5.5 Hz, 2H), 4.87 (s, 2H), 6.45 (m, 2H), 6.77 (d, J=8.7 Hz, 2H), 6.87 (dd, J=2.2, 8.8 Hz, 1H), 7.01 (d, J=9.1 Hz, 1H), 7.23 (d, J=2.2 Hz, 1H), 7.51 (d, J=8.8 Hz, 1H), 7.60 (d, J=8.7 Hz, 2H); MS (FD) m/e 488 ($MH^+$); HRMS (FAB) m/e calc'd. for $C_{29}H_{30}N_1O_4S_1$: 488.1896, found: 488.1911.

Example 17

[2-(2,4-Dimethoxyphenyl)-6-methoxybenzo[b]thien-3-yl] [4-[2-(1-piperidinyl)ethoxy]phenyl]methanone

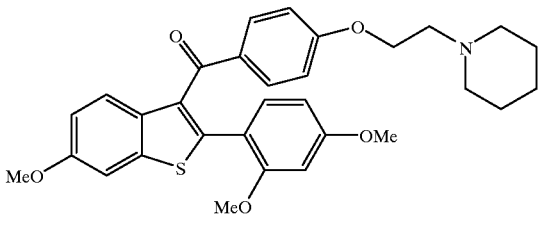

By the method described in Example 1, [2-dimethylamino-6-methoxybenzothien-3-yl][4-[2-(1-piperidinyl)ethoxy]phenyl]-methanone (2.0 g, 4.6 mmol) in THF (17 mL) was treated with a 1.8 M THF solution of 2,4-dimethoxyphenylmagnesium bromide (12.5 mL, 22.5 mmol) (prepared from 2,4-dimethoxybromobenzene, catalytic iodine, and magnesium turnings) to provide, after chromatography (silica gel, 1:1 hexane:ethyl acetate, 0–10% MeOH) 1.43 g (58%) of the title compound as a pale green, fluffy solid: $^1$H NMR d 1.44 (m, 2H), 1.60 (m, 4H), 2.49 (m, 4H), 2.74 (t, J=6.0 Hz, 2H), 3.49 (s, 3H), 3.75 (s, 3H), 3.87 (s, 3H), 4.07 (t, J=6.0 Hz, 2H), 6.21 (d, J=2.2 Hz, 1H), 6.42 (dd, J=2.3, 8.5 Hz, 1H), 6.74 (d, J=8.8 Hz, 2H), 6.95 (dd, J=2.3, 8.9 Hz, 1H), 7.30–7.33 (m, 2H), 7.63 (d, J=8.9 Hz, 1H), 7.74 (d, J=8.7 Hz, 2H); $^{13}$C NMR d 24.2, 26.0, 54.7, 55.2, 55.5, 55.7, 57.9, 66.3, 98.6, 104.4, 104.8, 113.8, 114.7, 115.7, 124.6, 130.7, 131.4, 132.0, 132.2, 133.7, 140.1, 140.4, 157.1, 157.5, 161.5, 162.5, 192.0; IR ($CHCl_3$) 1644, 1601 $cm^{-1}$; MS (FD) m/e 531 ($M^+$); Anal. calc'd. for $C_{31}H_{33}NO_5S$: C, 70.03; H, 6.26; N, 2.63. Found: C, 70.24; H, 6.35; N, 2.66.

Example 18

[2-(4-Hydroxy-2-methoxyphenyl)-6-hydroxybenzo[b]thien-3-yl] [4-[2-(1-piperidinyl)ethoxy]phenyl]methanone

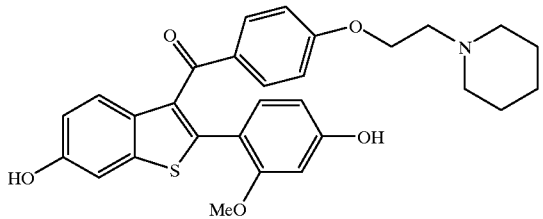

By the method described in Example 2, the product of Example 17 (1.24 g, 2.3 mmol), ethanethiol (1.1 mL, 15.0 mmol), and aluminum chloride (1.59 g, 12.0 mmol) were stirred in anhydrous $CH_2Cl_2$ (16 mL) to give, after chromatography (silica gel, 1:1 hexane:ethyl acetate, 1–10% MeOH) 0.17 g (15%) of the title product as a bright yellow solid: $^1$H NMR (1:1 $CDCl_3$/MeOD-$d_4$) d 1.44 (m, 2H), 1.59 (m, 4H), 2.49 (m, 4H), 2.73 (t, J=5.7 Hz, 2H), 3.43 (s, 3H), 4.07 (t, J=5.7 Hz, 2H), 6.11 (d, J=2.1 Hz, 1H), 6.31 (dd, J=2.2, 8.5 Hz, 1H), 6.72 (d, J=8.8 Hz, 2H), 6.84 (dd, J=2.3, 8.8 Hz, 1H), 7.16 (d, J=8.3 Hz, 1H), 7.21 (d, J=2.1, 1H), 7.53 (d, J=8.9 Hz, 1H), 7.68 (d, J=8.7 Hz, 2H); $^{13}$C NMR (1:1 $CDCl_3$/MeOD-$d_4$) d 24.3, 25.8, 54.7, 55.4, 58.1, 60.7, 65.9, 99.4, 104.4, 107.2, 108.0, 114.2, 114.7, 115.3, 124.5, 131.1, 132.5, 132.8, 133.4, 141.1, 141.4, 155.3, 157.6, 159.9, 163.1, 194.1; IR (KBr) 1612, 1597 $cm^{-1}$; MS (FD) m/e 504 ($MH^+$); HRMS (FAB) m/e calc'd for $C_{29}H_{30}NO_5S$ ($MH^+$): 504.1845, found: 504.1875; Anal. calc'd for $C_{29}H_{29}NO_5S \cdot \frac{1}{2}H_2O$: C, 67.82; H, 6.08; N, 2.73. Found: C, 67.52; H, 5.95; N, 2.94.

Example 19

[2-(4-Trifluoromethylphenyl)-6-methoxybenzo[b]thien-3-yl][4-[2-(1-piperidinyl)ethoxy]phenyl]methanone

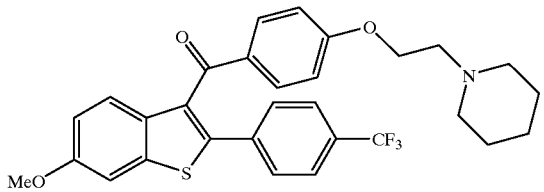

By the method described in Example 1, [2-dimethylamino-6-methoxybenzothien-3-yl][4-[2-(1-piperidinyl)ethoxy]phenyl]-methanone (1.0 g, 2.28 mmol) in THF (20 mL) was treated with a 0.69 M THF solution of 4-trifluoromethylphenylmagnesium bromide (10 mL, 6.9 mmol) (prepared from 4-bromobenzotrifluoride, catalytic iodine, and magnesium turnings in THF) to provide, after radial chromatography (silica gel, 4:1:.05–3:1:.05 hexane::ethyl acetate:MeOH, under an ammonia atmosphere) 991 mg (81%) of the title compound as a yellow oil: $^1$H NMR d 1.45 (m, 2H), 1.63 (m, 4H), 2.54 (m, 4H), 2.79 (t, J=5.8 Hz, 2H), 3.89 (s, 3H), 4.13 (t, J=5.8 Hz, 2H), 6.78 (d, J=8.8 Hz, 2H), 6.98 (dd, J=8.9, 2.3 Hz, 1H), 7.34 (d, J=2.2 Hz, 1H), 7.48 (d, J=8.4 Hz, 2H), 7.54 (d, J=8.4 Hz, 2H), 7.75 (d, J=8.8 Hz, 2H); $^{13}$C NMR d 24.0, 25.7, 55.0, 55.6, 57.6, 66.1, 104.4, 114.4, 115.3, 115.8, 124.5, 125.5 (q, J=3.0 Hz), 129.1, 130.2, 132.3, 133.2, 133.6, 137.3, 139.7, 140.6, 158.2, 163.3, 192.6; MS (FD+) m/e 539 ($M^+$); Anal. calc'd. for $C_{30}H_{28}F_3NO_3S$: C, 66.77; H, 5.24; N, 2.60. Found: C, 66.78; H, 5.30; N, 2.43.

Example 20

[2-(4-Trifluoromethylphenyl)-6-hydroxybenzo[b]thien-3-yl][4-[2-(1-piperidinyl)ethoxy]phenyl]methanone

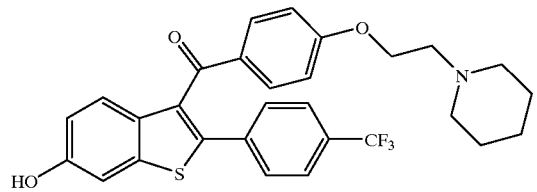

The product of Example 19 (480 mg, 0.89 mmol) was dissolved in anhydrous $CH_2Cl_2$ (15 mL), cooled to –78° C., and treated with a 1.0 M $CH_2Cl_2$ solution of boron tribromide (0.8 mL, 0.8 mmol). The mixture was allowed to warm to room temperature, stirred overnight, and treated with additional boron tribromide (1.75 mL, 1.75 mmol) in 2 portions. After 72 h, the mixture was diluted with 75 mL of water and extracted with $CH_2Cl_2$ (2×75 mL). The organic layers were washed with 2 N sodium hydroxide and the resultant aqueous layer was acidified and extracted with $CH_2Cl_2$ (75 mL). The combined organic layers were dried ($Na_2SO_4$), concentrated, and purified via radial chromatography (2:1:0.1 hexane:ethyl acetate:MeOH, under an ammonia atmosphere) to provide 110 mg (24%) of the title product as an amorphous green solid: $^1$H NMR d 1.45 (m, 2H), 1.63 (m, 4H), 2.57 (m, 4H), 2.79 (t, J=4.9 Hz, 2H), 4.08 (t, J=4.9 Hz, 2H), 6.59 (d, J=8.6 Hz, 2H), 6.77 (d, J=8.7 Hz, 1H), 7.15 (s, 1H), 7.33 (d, J=8.7 Hz, 1H), 7.42 (s, 4H), 7.64 (d, J=8.6 Hz, 2H), 8.18 (b, 1H); HRMS (FD+) m/e calc'd. for $C_{29}H_{27}F_3NO_3S$ ($MH^+$): 526.1664, found: 526.1669; Anal. calc'd for $C_{29}H_{26}F_3NO_3S \cdot H_2O$: C, 64.07; H, 5.20; N, 2.57. Found: C, 63.67; H, 5.12; N, 2.89.

Example 21

[2-(3-Fluorophenyl)-6-methoxybenzo[b]thien-3-yl][4-[2-(1-piperidinyl)ethoxy]phenyl]methanone

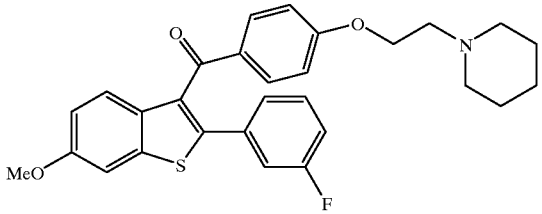

By the method described in Example 1, [2-dimethylamino-6-methoxybenzothien-3-yl][4-[2-(1-piperidinyl)ethoxy]phenyl]-methanone (1.5 g, 3.4 mmol) in THF (13 mL) was treated with a 1.9 M THF solution of 3-Fluorophenylmagnesium bromide (9.0 mL, 17 mmol) to provide, after chromatography (silica gel, 1:1 hexane:ethyl acetate, 0–10% MeOH) 1.13 g (68%) of the title compound as an off-white solid: $^1$H NMR d 1.44 (m, 2H), 1.58 (m, 4H), 2.47 (m, 4H), 2.73 (t, J=6.0 Hz, 2H), 3.89 (s, 3H), 4.08 (t, J=6.0 Hz, 2H), 6.78 (d, J=8.8 Hz, 2H), 6.87–6.93 (m, 1H), 6.97 (dd, J=2.3, 8.9 Hz, 1H), 7.11–7.20 (m, 3H), 7.33 (d, J=2.3 Hz, 1H), 7.53 (d, J=8.9 Hz, 1H), 7.75 (d, J=8.8 Hz, 2H); $^{13}$C NMR d 24.2, 25.9, 55.1, 55.7, 57.7, 66.3, 104.3, 104.5, 114.3, 115.15, 115.22, 115.4, 124.4, 124.6, 124.8, 130.3, 132.2, 132.4, 133.7, 140.4, 158.1, 160.9, 163.3, 164.2, 192.8; IR (CHCl$_3$) 1648, 1599 cm$^{-1}$; MS (FD) m/e 489 (M$^+$); Anal. calc'd. for $C_{29}H_{28}FNO_3S$: C, 71.14; H, 5.76; N, 2.86. Found: C, 70.89; H, 5.83; N, 2.85.

Example 22

[2-(3-Fluorophenyl)-6-hydroxybenzothien-3-yl] [4-[2-(1-piperidinyl)ethoxy]phenyl]methanone

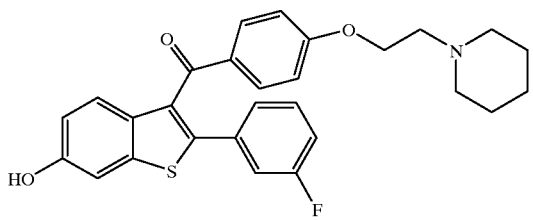

By the method described in Example 2, the product of Example 21 (0.57 g, 1.2 mmol), ethanethiol (1.1 mL, 15.0 mmol), and aluminum chloride (1.53 g, 11.0 mmol) were reacted in anhydrous CH$_2$Cl$_2$ (10 mL) to give, after chromatography (silica gel, 1:1 hexane:ethyl acetate 0–10% MeOH) 0.31 g (53%) of the title product as a bright yellow flaky solid: $^1$H NMR d 1.47 (m, 2H), 1.67 (m, 4H), 2.60 (m, 4H), 2.82 (t, J=5.4 Hz, 2H), 4.11 (t, J=5.4 Hz, 2H), 6.56 (d, J=8.9 Hz, 2H), 6.76 (dd, J=2.1, 8.8 Hz, 1H), 6.83–6.90 (m, 1H), 7.04–7.19 (m, 4H), 7.34 (d, J=8.8 Hz, 1H), 7.64 (d, J=8.8 Hz, 2H); $^{13}$C NMR (CDCl$_3$+DMSO-d$_6$) d 24.0, 25.8, 55.0, 57.6, 66.1, 107.1, 114.3, 114.9, 115.2, 115.5, 115.6, 115.8, 124.3, 124.6, 130.2, 132.2, 132.7, 135.7, 140.4, 155.9, 160.8, 163.1, 164.1, 193.0; IR (CHCl$_3$) 1649, 1599 cm$^{-1}$; MS (FD) m/e 476 (MH$^+$); HRMS (FD) m/e calc'd for $C_{28}H_{27}FNO_3S$ (MH$^+$): 476.1705, found: 476.1696.

Example 23

[2-(2-Methylphenyl)-6-hydroxybenzo[b]thien-3-yl] [4-[2-(1-piperidinyl)ethoxy]phenyl]methanone

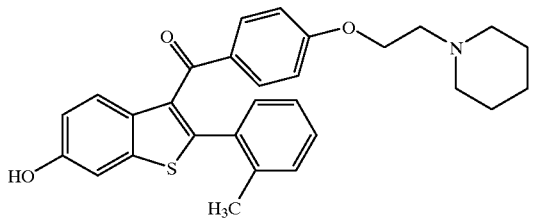

By the method described in Example 1, [2-dimethylamino-6-methoxybenzothien-3-yl][4-[2-(1-piperidinyl)ethoxy]phenyl]-methanone (1.5 g, 3.4 mmol) in THF (13 mL) was treated with a 1.9 M THF solution of 2-methylphenylmagnesium bromide (18 mL, 34.2 mmol) to provide, after chromatography (silica gel, 1:1 hexane:ethyl acetate, 0–10% MeOH) 0.811 g (49%) of a partially purified off-white, amorphous solid: $^1$H NMR d 1.5 (m, 2H), 1.7 (m, 4H), 2.4 (s, 3H), 2.6 (m, 4H), 2.8 (t, 2H), 4.0 (s, 3H), 4.2 (t, 2H), 6.8 (d, 2H), 7.0 (dd, 1H), 7.1–7.2 (m, 3H), 7.3–7.4 (m, 1H), 7.5 (d, 1H), 7.7 (d, 1H), 7.8 (d, 2H).

By the method described in Example 2, the crude product obtained above (0.83 g, 1.7 mmol), ethanethiol (0.95 mL, 13.0 mmol), and aluminum chloride (1.56 g, 12.0 mmol) were stirred in anhydrous CH$_2$Cl$_2$ (16 mL) to give, after chromatography (silica gel, 1:1 hexane:ethyl acetate, 0–10% methanol) 0.29 g (36%) of the title product as a pale yellow solid: $^1$H NMR d 1.48 (m, 2H), 1.66 (m, 4H), 2.23 (s, 3H), 2.58 (m, 4H), 2.80 (t, J=5.6 Hz, 2H), 4.09 (t, J=5.6 Hz, 2H), 6.57 (d, J=8.8 Hz, 2H), 6.82 (dd, J=2.1, 8.8 Hz, 1H), 7.01–7.13 (m, 3H), 7.17–7.24 (m, 2H), 7.48 (d, J=8.8 Hz, 1H), 7.61 (d, J=8.7 Hz, 2H); $^{13}$C NMR d 20.5, 23.9, 25.2, 54.9, 57.7, 65.1, 103.7, 107.3, 113.8, 115.5, 124.5, 125.4, 128.7, 130.2, 130.8, 131.1, 132.1, 132.8, 133.1, 137.1, 140.9, 142.9, 154.9, 162.4, 192.5; IR (CHCl$_3$) 1645, 1600 cm$^{-1}$; MS (FD) m/e 472 (MH$^+$); HRMS (FAB) m/e calc'd for $C_{29}H_{30}NO_3S$ (MH$^+$): 472.1946, found: 472.1942; Anal. calc'd for $C_{29}H_{29}NO_3S \cdot 0.5 H_2O$: C, 72.47; H, 6.29; N, 2.91. Found: C, 72.34; H, 6.16; N, 3.03.

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.70° C. with a minimum relative humidity of 40%. The photoperiod in the room was 12 hours light and 12 hours dark.

Dosing Regimen Tissue Collection.

After a one week acclimation period (therefore, two weeks post-OVX) daily dosing with test compound was initiated. 17a-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with CO$_2$, the uterus was removed through a midline incision, and a wet uterine weight was determined.

Cholesterol Analysis.

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotemetrically at 500 nm. Cholesterol concentration was then calculated against a standard curve. The entire assay was automated using a Biomek Automated Workstation.

Uterine Eosinophil Peroxidase (EPO) Assay.

Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound:

17a-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17a-ethynyl estradiol ($EE_2$; an orally available form of estrogen), and rats treated with certain compounds of the instant invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound | Dose mg/kg[a] | Uterine weight[b] (% increase vs. OVX) | Uterine EPO ($V_{max}$)[c] | Serum Cholesterol[d] (% decrease vs. OVX) |
|---|---|---|---|---|
| $EE_2$[e] | 0.1 | 86.3 | 116.4 | 81.4 |
| Example 2 | 0.01 | 3.2 | 4.8 | 21.7 |
|  | 0.1 | 53.3 | 4.8 | 48.1 |
|  | 1.0 | 53.7 | 4.8 | 64.7 |
|  | 10.0 | 25.9 | 3.6 | 47.8 |
| Example 5 | 0.1 | −22.6 | 1.2 | 18.6 |
|  | 1.0 | 20.7 | 2.4 | 52.6 |
|  | 10.0 | 30.2 | 1.3 | 71.5 |
| Example 7 | 0.1 | 7.6 | 4.9 | 53.7 |
|  | 1.0 | 15.6 | 2.5 | 77.6 |
|  | 10.0 | 24.6 | 2.8 | 49.7 |
| Example 8 | 0.1 | −8.3 | 1.3 | 24.8 |
|  | 1.0 | 23.4 | 4.4 | 57.8 |
|  | 10.0 | 24.1 | 11.2 | 60.8 |
| Example 10 | 0.1 | −18.3 | 2.8 | 7.8 |
|  | 1.0 | −21 | 1.7 | 19.5 |
|  | 10.0 | 10.6 | 3.7 | 33.2 |
| Example 12 | 0.1 | 15.5 | 2.0 | 24.3 |
|  | 1.0 | 22.7 | 2.6 | 52.3 |
|  | 10.0 | 16.7 | 2.4 | 49.1 |
| Example 13 | 0.1 | −18.6 | 3.0 | 25.3 |
|  | 1.0 | 34.7 | 6.0 | 45.7 |
|  | 10.0 | 27.6 | 8.4 | 61.4 |

TABLE 1-continued

| Compound | Dose mg/kg[a] | Uterine weight[b] (% increase vs. OVX) | Uterine EPO ($V_{max}$)[c] | Serum Cholesterol[d] (% decrease vs. OVX) |
|---|---|---|---|---|
| Example 16 | 0.1 | 54.5 | 8.1 | 39.2 |
|  | 1.0 | 53.7 | 8.4 | 62.6 |
|  | 10.0 | 62.7 | 8.1 | 68.5 |
| Example 17 | 0.1 | 40.1 | 20.4 | 51.4 |
|  | 1.0 | 66.1 | 102.0 | 68.5 |
|  | 10.0 | 53.7 | 20.1 | 67.2 |
| Example 18 | 0.1 | 64.1 | 34.2 | 58.8 |
|  | 1.0 | 69.2 | 81.9 | 79.0 |
|  | 10.0 | 73.3 | 135.9 | 71.6 |
| Example 19 | 0.1 | 10.3 | 6.8 | 22.3 |
|  | 1.0 | 15.6 | 4.3 | 3.1 |
|  | 10.0 | 16.6 | 4 | 20.6 |
| Example 20 | 0.1 | −2 | 1.8 | 45.5 |
|  | 1.0 | 7 | 7 | 47.9 |
|  | 5.0 | 37.4 | 16.4 | 71.5 |
| Example 21 | 0.1 | 14.9 | 4.5 | 1.4 |
|  | 1.0 | 4.1 | 4.8 | −12 |
|  | 10.0 | 25.3 | 7.5 | 60.5 |
| Example 22 | 0.1 | 53.2 | 4.8 | 18.6 |
|  | 1.0 | 62.8 | 7.8 | 62.0 |
|  | 10.0 | 26.9 | 12.0 | 67.3 |
| Example 23 | 0.1 | 8.5 | 12.0 | 31.7 |
|  | 1.0 | 12 | 8.4 | 38.6 |
|  | 10.0 | 10.9 | 8.1 | 29.3 |

[a]mg/kg PO
[b]Uterine Weight % increase versus the ovariectomized controls
[c]Eosinophil peroxidase, $V_{maxium}$
[d]Serum cholesterol decrease versus ovariectomized controls
[e]17-a-Ethynyl-estradiol
* $p < .05$ In addition to the demonstrated benefits of the compounds of the instant invention, the above data clearly demonstrate that compounds of Formula I are not estrogen mimetics. Furthermore, no deleterious toxicological effects (for example, survival numbers) were observed with any treatment.

Osteoporosis Test Procedure

Following the General Preparation Procedure, infra, the rats were treated daily for 35 days (6 rats per treatment group) and sacrificed by carbon dioxide asphyxiation on the 36th day. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

The right femurs were excised and digitilized x-rays generated and analyzed by an image analysis program (NIH image) at the distal metaphysis. The proximal aspect of the tibiae from these animals were also scanned by quantitative computed tomography.

In accordance with the above procedures, compounds of the instant invention and ethynyl estradiol ($EE_2$) in 20% hydroxypropyl b-cyclodextrin were orally administered to test animals. Distal femur metaphysis and proximal tibiae data presented in Tables 2 and 3 below, respectively are the results of formula I compound treatments compared to intact and ovariectomized test animals. Results are reported as percent protection relative to ovariectomy.

TABLE 2

| Compound/Treatment | Dose mg/kg | Distal Femur Metaphysis (X-ray Image Analysis- Gray Score) |
|---|---|---|
| EE2 |  | 80.7* |
| Example 2 | 0.01 | 34.5 |
|  | 0.1 | 34.1 |
|  | 1.0 | 68.0* |
|  | 10.0 | 70.0* |

*P <= 0.5 two tailed Student's T Test on raw data

TABLE 3

| Compound/Treatment | Dose mg/kg | Proximal Tibiae Total Bone Mineral Density (Quantitative Computed Tomography) |
|---|---|---|
| EE2 | 0.1 | 59.4* |
| Example 12 | 0.1 | −30.9 |
|  | 1.0 | 51.5* |
|  | 10.0 | 79.7* |

*P <= 0.5 two tailed Student's T Test on raw data

In summary, ovariectomy of the test animals caused a significant reduction in femur density compared to intact, vehicle treated controls. Orally administered ethynyl estradiol ($EE_2$) prevented this loss, but the risk of uterine stimulation with this treatment is ever-present.

The compounds of the instant invention also prevented bone loss in a general, dose-dependent manner. Accordingly, the compounds of the instant invention are useful for the treatment of osteoporosis, particularly caused by postmenopausal syndrome.

MCF-7 Proliferation Assay

MCF-7 breast adenocarcinoma cells (ATCC HTB 22) were maintained in MEM (minimal essential medium, phenol red-free, Sigma, St. Louis, Mo.) supplimented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium (Ca++/Mg++ free HBSS (phenol red-free) supplemented with 10 mM HEPES and 2 mM EDTA). Cells were washed twice with assay medium and adjusted to 80,000 cells/mL. Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallac BetaPlace b counter. Results in Table 4 below show the $IC_{50}$ for certain compounds of the instant invention. Cultures were terminated by freezing at −70° C. for 24 hours followed by thawing and harvesting of microcultures using a Skatron Semiautomatic Cell Harvester. Samples were counted by liquid scintillation using a Wallac BetaPlace b counter. Results in Table 4 below show the $IC_{50}$ for certain compounds of the instant invention.

TABLE 4

| Compound (Example Reference) | $IC_{50}$ nM |
|---|---|
| 2 | 0.3 |
| 5 | 2.3 |
| 7 | 1 |
| 10 | 10 |
| 12 | 3.2 |
| 16 | 2 |
| 17 | 300 |
| 18 | 2 |
| 19 | Not active at the concentrations tested |
| 20 | 1000 |
| 21 | 500 |
| 22 | 2.5 |
| 23 | 0.7 |

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenzo[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

We claim:
1. A compound of formula I:

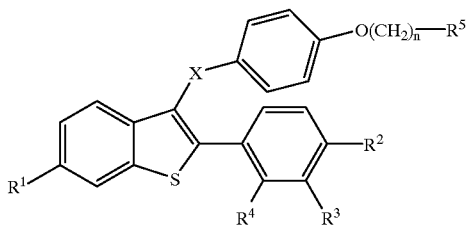

wherein:

X is —CH₂—, —CH(OH)—, or —CO—;

R¹ is —H, —OH, —O(C₁–C₄ alkyl), —OCOAr where Ar is phenyl or substituted phenyl, —OCO(C₁–C₆ alkyl), or —OSO₂(C₄–C₆ alkyl);

R², R³, and R⁴ are, independently, —R¹, —F, —Cl, C₁–C₄ alkyl, or —CF₃, with the proviso that at least one of R², R³, and R⁴ is —CF₃ or —OSO₂(C₄–C₆ alkyl) and with the further proviso that when R² is —OSO₂(C₄–C₆ alkyl) then R³ and R⁴ are not both hydrogen;

n is 2 or 3; and

R⁵ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt or solvate thereof.

2. A compound according to claim 1 wherein X is —CO—.

3. A compound according to claim 2 wherein n is two.

4. A compound according to claim 3 wherein R² is methoxy.

5. A compound according to claim 3 wherein R² is hydroxy.

6. A compound according to claim 5 wherein R₄ is hydrogen and R³ is fluoro.

7. A compound according to claim 5 wherein R⁴ is methyl and R³ is hydrogen.

8. A compound according to claim 5 wherein R⁴ is methoxy and R³ is hydrogen.

9. A compound according to claim 3 wherein R² and R⁴ are hydrogen and R³ is methoxy.

10. A compound according to claim 3 wherein R² and R⁴ are hydrogen and R³ is hydroxy.

11. A compound according to claim 3 wherein R⁴ and R³ are hydrogen and R² is trifluoromethyl.

12. A compound according to claim 3 wherein R₄ is hydrogen, R³ is fluoro, and R² is methoxy.

13. A compound of formula VII:

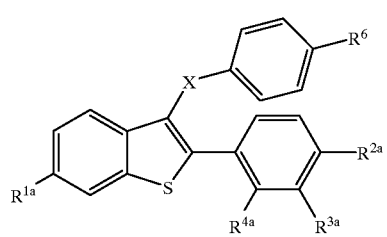

wherein:

X is —CO—, —CHOH—, or —CH₂—;

R¹ᵃ is —H or —OR⁷, where R⁷ is a hydroxy protecting group;

R²ᵃ, R³ᵃ, R⁴ᵃ are, independently, —H, —OR⁷, —F, —Cl, C₁–C₄ alkyl, or —CF₃, with the proviso that at least one of R²ᵃ, R³ᵃ, and R⁴ᵃ is —CF₃ or —OSO₂(C₄–C₆ alkyl) and with the further proviso that when R²ᵃ is —OSO₂(C₄–C₆ alkyl) then R³ᵃ and R⁴ᵃ are not both hydrogen; and R⁶ is —OCH₃ or —OH.

14. A compound according to claim 13 wherein R⁷ is methyl.

15. A compound according to claim 14 wherein X is —CO—.

16. A compound according to claim 15 wherein R⁶ is —OCH₃.

17. A compound according to claim 15 wherein R⁶ is —OH.

18. A compound of formula IX:

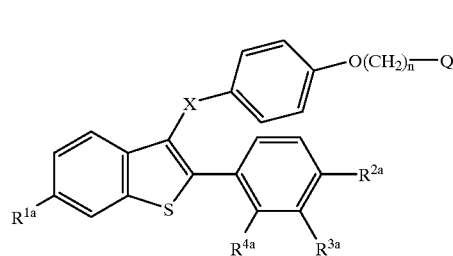

wherein:

X is —CO—, —CHOH—, or —CH₂—;

R¹ᵃ is —H or —OR⁷, where R⁷ is a hydroxy protecting group;

R²ᵃ, R³ᵃ, R⁴ᵃ are, independently, —H, —OR⁷, —F, —Cl, C₁–C₄ alkyl, or —CF₃, with the proviso that at least one of R²ᵃ, R³ᵃ, and R⁴ᵃ is —CF₃ or —OSO₂(C₄–C₆ alkyl) and with the further proviso that when R²ᵃ is —OSO₂(C₄–C₆ alkyl) then R³ᵃ and R⁴ᵃ are not both hydrogen;

n is 2 or 3; and

Q is a leaving group.

19. A compound according to claim 18 wherein Q is bromo.

20. A compound according to claim 19 wherein n is two.

21. A compound according to claim 20 wherein X is —CO—.

22. A compound of formula XI:

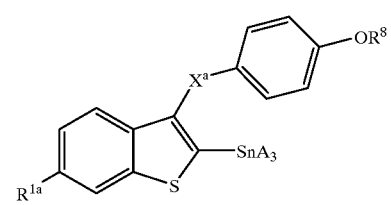

wherein:

Xᵃ is —CO—;

R¹ᵃ is —H or —OR⁷, where R⁷ is a hydroxy protecting group;

$R^8$ is —$CH_3$ or –$(CH_2)_nR^5$;

n is 2 or 3;

$R^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and A is $C_1$–$C_4$ alkyl or phenyl.

23. A compound according to claim 22 wherein A is methyl.

24. A compound according to claim 23 wherein $R^8$ is –$(CH_2)_nR^5$.

25. A method of inhibiting bone loss or bone resorption which comprises administering to a patient in need thereof an effective amount of a compound of claim 1.

26. A method according to claim 25, wherein said bone loss or bone resorption is due to menopause or ovariectomy.

27. A method of lowering serum cholesterol levels which comprises administering to a patient in need thereof an effective amount of a compound of claim 1.

28. A compound according to claim 1 selected from the group consisting of

[2-(4-Trifluoromethylphenyl)-6-methoxybenzo[b]thien-3-yl][4-[2-(1-piperidinyl)ethoxy]phenyl]methanone;

[2-(4-Trifluoromethylphenyl)-6-hydroxybenzo[b]thien-3-yl][4-[2-(1-piperidinyl)ethoxy]phenyl]methanone;

[2-(3-n-butylsulfonoyloxyphenyl)-6-n-butylsulfonoyloxybenzo[b]thien-3-yl][4-[2-(1-piperidinyl)ethoxy]phenyl]methanone.

\* \* \* \* \*